United States Patent
Vogelstein et al.

(10) Patent No.: US 9,670,527 B2
(45) Date of Patent: Jun. 6, 2017

(54) ENRICHMENT OF NUCLEIC ACIDS BY COMPLIMENTARY CAPTURE

(75) Inventors: Bert Vogelstein, Balitmore, MD (US); Kenneth W. Kinzler, Baltimore, MD (US); Nickolas Papadopoulos, Towson, MD (US); Jian Wu, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 252 days.

(21) Appl. No.: 14/130,007

(22) PCT Filed: Jun. 28, 2012

(86) PCT No.: PCT/US2012/044634
§ 371 (c)(1),
(2), (4) Date: Jan. 29, 2014

(87) PCT Pub. No.: WO2013/003585
PCT Pub. Date: Jan. 3, 2013

(65) Prior Publication Data
US 2014/0154683 A1    Jun. 5, 2014

Related U.S. Application Data

(60) Provisional application No. 61/502,622, filed on Jun. 29, 2011.

(51) Int. Cl.
*C12Q 1/68* (2006.01)

(52) U.S. Cl.
CPC .................................. *C12Q 1/6806* (2013.01)

(58) Field of Classification Search
None
See application file for complete search history.

(56) References Cited

U.S. PATENT DOCUMENTS

| | | |
|---|---|---|
| 2008/0254516 A1 | 10/2008 | St. John et al. |
| 2009/0099041 A1 | 4/2009 | Church et al. |

FOREIGN PATENT DOCUMENTS

| | | |
|---|---|---|
| EP | 0421469 A2 | 4/1991 |
| WO | 2010-117817 A2 | 10/2010 |

*Primary Examiner* — David Thomas
(74) *Attorney, Agent, or Firm* — Banner & Witcoff, LTD.

(57) ABSTRACT

Assays can be used to detect mutations found in neoplasms of the pancreas, as well as for other neoplasms and other uses. Nucleic acids can be captured from body fluids such as cyst fluids. Thousands of oligonucleotides can be synthesized in parallel, amplified and ligated together. The ligated products can be further amplified. The amplified, ligated products are used to capture complementary DNA sequences, which can be analyzed, for example by massively parallel sequencing.

22 Claims, 17 Drawing Sheets

Table S1. Genes analyzed by massively parallel sequencing in IPMN cyst fluids.

| Gene symbol | Accession Number | Oncogene or Tumor Suppressor Gene |
|---|---|---|
| ABL1 | X16416 | Oncogene |
| ARHGAP29 | NM_004815.2 | Suppressor Gene |
| AKT1 | NM_005163 | Oncogene |
| ALK | NM_004304 | Oncogene |
| JARID1C | NM_004187.1 | Suppressor Gene |
| APC | NM_000038 | Suppressor Gene |
| ATM | NM_000051 | Suppressor Gene |
| UBR4 | NM_020765.1 | Suppressor Gene |
| BRAF | NM_004333 | Oncogene |
| BRCA1 | NM_007294.1 | Suppressor Gene |
| BRCA2 | NM_000059.1 | Suppressor Gene |
| CBL | NM_005188.1 | Oncogene |
| CDC73 | NM_024529.3 | Suppressor Gene |
| CDH1 | NM_004360.2 | Suppressor Gene |
| CDKN2A | NM_000077 | Suppressor Gene |
| CEBPA | NM_004364.2 | Suppressor Gene |
| CSF1R | NM_005211 | Oncogene |
| CTNNA1 | NM_001903.2 | Suppressor Gene |
| CTNNB1 | NM_001904 | Oncogene |
| ATR | NM_001184 | Suppressor Gene |
| CYLD | NM_015247.1 | Suppressor Gene |
| LRRK2 | SU_LRRK2 | Suppressor Gene |
| KIAA1409 | ENST00000256339 | Suppressor Gene |
| SPTAN1 | ENST00000372731 | Suppressor Gene |
| ATRX | NM_138271.1 | Suppressor Gene |
| SPEG | SU_SPEG | Suppressor Gene |
| MAST4 | SU_MAST4 | Suppressor Gene |
| DPYSL4 | ENST00000338492 | Oncogene |
| EGFL6 | NM_015507.2 | Oncogene |
| EGFR | NM_005228 | Oncogene |
| WNK2 | SU_WNK2 | Suppressor Gene |
| CAD | NM_004341.2 | Suppressor Gene |
| SORL1 | ENST00000260197 | Suppressor Gene |
| NUP214 | NM_005085.2 | Suppressor Gene |
| ERBB2 | NM_004448 | Oncogene |
| TECTA | ENST00000392793 | Suppressor Gene |
| ADAMTS20 | NM_025003.2 | Suppressor Gene |
| TRIP11 | ENST00000267622 | Suppressor Gene |
| FAM123B | NM_152424.1 | Suppressor Gene |
| FBXW7 | NM_033632.1 | Suppressor Gene |
| TAF1 | NM_138923 | Suppressor Gene |
| FGFR3 | NM_000142 | Oncogene |
| FLT3 | Z26652 | Oncogene |

FIG. 5A

| Gene | Accession | Type |
|---|---|---|
| COL14A1 | NM_021110.1 | Suppressor Gene |
| FOXL2 | NM_023067.2 | Oncogene |
| NUP98 | NM_016320.2 | Suppressor Gene |
| GATA1 | NM_002049.2 | Suppressor Gene |
| CDC42BPB | NM_006035 | Suppressor Gene |
| LTBP1 | NM_206943.1 | Suppressor Gene |
| TAF1L | NM_153809 | Suppressor Gene |
| GNAQ | NM_002072.2 | Oncogene |
| GNAS | NM_000516.3 | Oncogene |
| ITSN2 | NM_006277.1 | Suppressor Gene |
| N4BP2 | NM_018177.2 | Suppressor Gene |
| JARID1A | NM_005056.1 | Suppressor Gene |
| DEPDC2 | NM_024870.2 | Suppressor Gene |
| HNF1A | NM_000545.3 | Suppressor Gene |
| HRAS | NM_005343 | Oncogene |
| IDH1 | NM_005896.2 | Oncogene |
| IDH2 | NM_002168.2 | Oncogene |
| GLI3 | NM_000168.2 | Suppressor Gene |
| CENTD3 | NM_022481.4 | Suppressor Gene |
| BAZ1A | NM_013448.2 | Suppressor Gene |
| MAP4K4 | NM_145686 | Suppressor Gene |
| COL1A1 | ENST00000225964 | Suppressor Gene |
| ASXL1 | ENST00000358956 | Suppressor Gene |
| JAK2 | NM_004972 | Oncogene |
| JAK3 | NM_000215 | Oncogene |
| ROCK2 | NM_004850 | Suppressor Gene |
| ROCK1 | NM_005406 | Suppressor Gene |
| IKBKAP | NM_003640.2 | Suppressor Gene |
| KIT | NM_000222 | Oncogene |
| IGF1R | NM_000875 | Suppressor Gene |
| KRAS | NM_004985 | Oncogene |
| STK36 | NM_015690 | Suppressor Gene |
| RAD50 | NM_133482.1 | Suppressor Gene |
| MAP3K6 | NM_004672 | Suppressor Gene |
| PER1 | ENST00000317276 | Suppressor Gene |
| WNK4 | NM_032387 | Suppressor Gene |
| MAP2K4 | NM_003010 | Suppressor Gene |
| ADAMTS18 | NM_199355.1 | Suppressor Gene |
| MGA | XM_031689.7 | Suppressor Gene |
| ABL2 | NM_005158 | Suppressor Gene |
| TSC1 | NM_000368.2 | Suppressor Gene |
| MEN1 | ENST00000312049 | Suppressor Gene |
| MET | NM_000245 | Oncogene |
| TNKS2 | AF264912.1 | Suppressor Gene |
| TNK2 | NM_005781 | Suppressor Gene |
| TRIM33 | NM_015906 | Suppressor Gene |

FIG. 5B

| | | |
|---|---|---|
| MLH1 | NM_000249.2 | Suppressor Gene |
| ULK2 | NM_014683 | Suppressor Gene |
| GUCY2F | NM_001522 | Suppressor Gene |
| HDAC4 | NM_006037.2 | Suppressor Gene |
| MPL | NM_005373.1 | Oncogene |
| MSH2 | NM_000251.1 | Suppressor Gene |
| MSH6 | NM_000179.1 | Suppressor Gene |
| ERN2 | NM_033266.1 | Suppressor Gene |
| USP24 | XM_371254.3 | Suppressor Gene |
| NF1 | ENST00000358273 | Suppressor Gene |
| NF2 | NM_000268.2 | Suppressor Gene |
| NFKB1 | NM_003998.2 | Suppressor Gene |
| EPHB1 | NM_004441 | Suppressor Gene |
| NOTCH1 | NM_017617.2 | Suppressor Gene |
| NOTCH2 | NM_024408.2 | Suppressor Gene |
| NPM1 | NM_002520.4 | Suppressor Gene |
| NRAS | NM_002524 | Oncogene |
| PHF14 | NM_001007157.1 | Suppressor Gene |
| ROR2 | NM_004560 | Suppressor Gene |
| TNPO1 | NM_002270.2 | Suppressor Gene |
| PDGFRA | NM_006206 | Oncogene |
| AXL | NM_001699 | Suppressor Gene |
| PRKD2 | NM_016457 | Suppressor Gene |
| TTK | NM_003318 | Suppressor Gene |
| PIK3CA | NM_006218.1 | Oncogene |
| TNNI3K | NM_015978 | Suppressor Gene |
| PRKAR1A | NM_212472.1 | Suppressor Gene |
| VEPH1 | ENST00000392832 | Suppressor Gene |
| HIF1A | NM_001530.2 | Suppressor Gene |
| PTCH1 | NM_000264.2 | Suppressor Gene |
| PTEN | NM_000314.4 | Suppressor Gene |
| PTPN11 | NM_002834.3 | Oncogene |
| PTPRC | NM_002838.2 | Oncogene |
| RPS6KA2 | NM_021135 | Suppressor Gene |
| BRD2 | NM_005104 | Suppressor Gene |
| ITGB3 | NM_000212.2 | Suppressor Gene |
| RB1 | NM_000321 | Suppressor Gene |
| RET | NM_020975 | Oncogene |
| ADAM29 | NM_014269.2 | Suppressor Gene |
| ANAPC5 | NM_016237.3 | Suppressor Gene |
| ITGB2 | NM_000211.1 | Suppressor Gene |
| CHUK | NM_001278 | Suppressor Gene |
| TCF12 | NM_207037.1 | Suppressor Gene |
| PDZRN4 | NM_013377.2 | Suppressor Gene |
| RUNX1 | ENST00000300305 | Suppressor Gene |
| SETD2 | ENST00000330022 | Suppressor Gene |

FIG. 5C

| | | |
|---|---|---|
| SMAD2 | NM_005901.3 | Suppressor Gene |
| SMAD4 | NM_005359.3 | Suppressor Gene |
| SMARCA4 | NM_003072.2 | Suppressor Gene |
| SMARCB1 | NM_003073.2 | Suppressor Gene |
| PAK7 | NM_020341 | Suppressor Gene |
| SMO | NM_005631.3 | Oncogene |
| APBB1IP | NM_019043.3 | Suppressor Gene |
| SOCS1 | NM_003745.1 | Suppressor Gene |
| PRKCA | NM_002737 | Suppressor Gene |
| NEK11 | NM_024800.2 | Suppressor Gene |
| TCF7L2 | ENST00000369397 | Suppressor Gene |
| STK11 | NM_000455 | Suppressor Gene |
| ITK | NM_005546 | Suppressor Gene |
| MAP3K2 | NM_006609 | Suppressor Gene |
| ACVR1B | NM_020328 | Suppressor Gene |
| CDC7 | NM_003503.2 | Suppressor Gene |
| TGFBR2 | NM_003242 | Suppressor Gene |
| SRC | NM_005417 | Suppressor Gene |
| TNFAIP3 | NM_006290.2 | Suppressor Gene |
| BMPR1A | NM_004329 | Suppressor Gene |
| ACVR2A | NM_001616 | Suppressor Gene |
| RAD18 | NM_020165.2 | Suppressor Gene |
| SUFU | NM_016169.2 | Suppressor Gene |
| TP53 | NM_000546 | Suppressor Gene |
| MAP2K7 | NM_005043 | Suppressor Gene |
| STK32B | NM_018401 | Suppressor Gene |
| TSHR | NM_000369.1 | Oncogene |
| MGC42105 | NM_153361 | Suppressor Gene |
| STK19 | NM_032454 | Suppressor Gene |
| UTX | NM_021140.1 | Suppressor Gene |
| VHL | NM_000551.2 | Suppressor Gene |
| LDHB | NM_002300.3 | Suppressor Gene |
| WT1 | NM_024426.2 | Suppressor Gene |
| PHOX2B | ENST00000381741 | Suppressor Gene |

FIG. 5D

Table S2. Characteristics of patients with IPMNs analyzed in this study, including GNAS and KRAS mutation status.

| IPMN # | KRAS mutation | GNAS mutation | Age at surgery | Sex | History of smoking | Post-operative diagnosis | Cyst Grade | Cyst diameter (cm) | Duct type | IPMN Subtype | Cyst location | Sample type |
|---|---|---|---|---|---|---|---|---|---|---|---|---|
| 1 | G12V | R201C | 71 | M | No | IPMN | intermediate | 3.0 | mixed | gastric | body/tail | Cyst wall |
| 2 | G12D | R201H | 68 | M | unknown | IPMN | high | 2.0 | branch | gastric | body/tail | Cyst wall |
| 3 | G12D | R201C | 69 | M | unknown | IPMN | intermediate | 2.0 | branch | gastric | head | Cyst wall |
| 4 | G12R | R201H | 73 | F | unknown | IPMN | high | 3.2 | main | pancreatobiliary | head | Cyst wall |
| 5 | G12D & G12R | No mutation detected | 66 | M | No | IPMN | intermediate | 4.0 | branch | gastric | entire pancreas | Cyst fluid |
| 6 | G12R | R201C | 63 | M | unknown | IPMN | high | 8.0 | mixed | intestinal | head | Cyst wall |
| 7 | No mutation detected | R201H | 64 | F | No | IPMN | high | 2.0 | branch | intestinal | body/tail | Cyst wall |
| 8 | G12V | R201C | 80 | M | No | IPMN | high | 2.0 | main | gastric | body/tail | Cyst wall |
| 9 | G12V & G12D | R201C & R201H | 74 | M | No | IPMN | high | 6.5 | main | pancreatobiliary | entire pancreas | Cyst wall |
| 10 | G12D | R201C | 39 | F | No | IPMN | low | 2.0 | branch | gastric | head | Cyst wall |
| 11 | G12D | No mutation detected | 67 | M | No | IPMN | high | 2.0 | main | gastric | head | Cyst wall |
| 12 | G12V | R201C | 70 | M | No | IPMN | high | 3.0 | branch | gastric | head | Cyst wall |
| 13 | G12V | R201H | 78 | M | No | IPMN | high | 3.0 | main | gastric | head | Cyst wall |
| 14 | G12R | R201C | 79 | M | No | IPMN | high | 5.0 | branch | gastric | head | Cyst wall |
| 15 | G12D | R201H | 84 | M | No | IPMN | low | 1.5 | branch | gastric | head | Cyst wall |
| 16 | G12V | P201C | 66 | F | No | IPMN | intermediate | 1.8 | branch | gastric | head | Cyst wall |
| 17 | G12D | R201C | 63 | F | Yes | IPMN | high | 1.8 | branch | gastric | body/tail | Cyst wall |
| 18 | G12D | R201H | 81 | M | Yes | IPMN | intermediate | 3.0 | not determined | gastric | head | Cyst wall |
| 19 | G12D | R201H | 69 | M | Yes | IPMN | low | 2.5 | not determined | gastric | head | Cyst wall |
| 20 | G12V | R201C | 70 | F | unknown | IPMN | high | 5.0 | mixed | not determined | body/tail | Cyst wall |
| 21 | No mutation detected | R201H | 80 | M | unknown | IPMN | high | 0.7 | main | gastric | body/tail | Cyst wall |
| 22 | No mutation detected | R201C | 50 | F | unknown | IPMN | low | 1.2 | mixed | intestinal | body/tail | Cyst wall |
| 23 | No mutation detected | R201H | 81 | M | Yes | IPMN | high | 2.5 | main | intestinal | body/tail | Cyst wall |
| 24 | G12V | R201C | 51 | F | No | IPMN | intermediate | 1.0 | mixed | gastric | head | Cyst wall |
| 25 | No mutation detected | R201H | 78 | M | unknown | IPMN | high | 3.0 | mixed | intestinal | head | Cyst wall |
| 26 | G12D | R201C | 70 | F | No | IPMN | intermediate | 1.4 | branch | not determined | body/tail | Cyst wall |
| 27 | G12V | R201H | 66 | F | No | IPMN | high | 2.7 | mixed | gastric | head | Cyst wall |
| 28 | G12D | No mutation detected | 92 | M | Yes | IPMN | intermediate | 0.5 | branch | gastric | head | Cyst wall |
| 29 | G12D & G12V | No mutation detected | 88 | F | No | IPMN | high | 3.5 | pancreatobiliary | body/tail | Cyst fluid |
| 30 | No mutation detected | R201H | 65 | M | Yes | IPMN | high | 6.5 | main | gastric | head | Cyst fluid |
| 31 | G12D & G12V & G12R | R201C | 79 | M | unknown | IPMN | high | 2.5 | branch | not determined | head | Cyst fluid |
| 32 | No mutation detected | No mutation detected | 74 | F | Yes | IPMN | high | 5.0 | mixed | pancreatobiliary | head | Cyst fluid |
| 33 | G12R | R201C | 82 | M | unknown | IPMN | high | 1.9 | main | not determined | head | Cyst fluid |
| 34 | G12V | R201H | 75 | M | No | IPMN | high | 2.0 | mixed | gastric | body/tail | Cyst fluid |
| 35 | G12V & G12D | R201C | 58 | F | No | IPMN | low | 0.8 | mixed | gastric | body | Cyst fluid |
| 36 | G12D | R201H | 69 | M | Yes | IPMN | low | 5.6 | branch | gastric | head | Cyst fluid |
| 37 | G12V | No mutation detected | 73 | F | unknown | IPMN | intermediate | 1.5 | mixed | gastric | body/tail | Cyst fluid |
| 38 | No mutation detected | No mutation detected | 46 | M | No | IPMN | intermediate | 2.8 | branch | not determined | head | Cyst fluid |
| 39 | No mutation detected | R201C | 60 | F | Yes | IPMN | high | 7.5 | main | not determined | head | Cyst fluid |
| 40 | G12R | No mutation detected | 75 | F | Yes | IPMN | low | 1.1 | mixed | not determined | tail | Cyst fluid |
| 41 | G12D | R201C | 72 | M | Yes | IPMN | low | 4.0 | branch | not determined | head | Cyst fluid |
| 42 | G12D | R201H | 66 | M | Yes | IPMN | intermediate | 1.9 | mixed | not determined | head | Cyst fluid |
| 43 | G12V | R201C | 76 | F | No | IPMN | high | 2.0 | mixed | not determined | body | Cyst fluid |
| 44 | G12D | R201H | 70 | M | Yes | IPMN | low | 0.8 | branch | not determined | head | Cyst fluid |
| 45 | No mutation detected | R201H | 85 | M | No | IPMN | intermediate | 4.5 | mixed | not determined | neck | Cyst fluid |
| 46 | No mutation detected | R201H | 72 | F | No | IPMN | low | 2.0 | branch | not determined | tail | Cyst fluid |
| 47 | G12R | R201C | 60 | F | No | IPMN | low | 2.9 | branch | not determined | tail | Cyst fluid |
| 48 | G12D | R201C & R201H | 84 | M | unknown | IPMN | high | 3.2 | mixed | not determined | body | Cyst fluid |
| 49 | G12D | R201C | 71 | F | unknown | IPMN | low | 3.0 | main | not determined | body | Cyst fluid |
| 50 | G12V | R201C | 70 | F | unknown | IPMN | intermediate | 3.0 | mixed | not determined | body | Cyst fluid |
| 51 | G12V | No mutation detected | 76 | F | unknown | IPMN | low | 3.4 | branch | not determined | body | Cyst fluid |

| | | | | | | | | | | | |
|---|---|---|---|---|---|---|---|---|---|---|---|
| 107 | G12D | No mutation detected | 71 | M | unknown | IPMN | low | 6.0 | branch | not determined | head | Cyst fluid |
| 108 | G12D | R201H | 66 | M | unknown | IPMN | intermediate | 0.6 | branch | intestinal | head | Cyst fluid |
| 109 | No mutation detected | R201H | 65 | F | unknown | IPMN | intermediate | 1.8 | mixed | gastric | head | Cyst fluid |
| 110 | G12V | R201C | 56 | M | unknown | IPMN | intermediate | 2 | main | gastric | head | Cyst fluid |
| 111 | G12V | No mutation detected | 63 | M | unknown | IPMN | intermediate | 3.1 | branch | gastric | head | Cyst fluid |
| 112 | G12R | R201C | 62 | M | unknown | IPMN | intermediate | 3.5 | branch | not determined | head | Cyst fluid |
| 113 | G12D | R201C | 71 | M | unknown | IPMN | low | 3.5 | branch | gastric | head | Cyst wall |
| 114 | G12R | No mutation detected | 60 | M | No | IPMN | high | 13.0 | mixed | pancreatobiliary | entire pancreas | Cyst wall |
| 115 | G12D | R201H | 70 | M | No | IPMN | high | 4.0 | main | pancreatobiliary | head | Cyst wall |
| 116 | No mutation detected | R201C | 62 | F | No | IPMN | high | 6.0 | main | gastric | head | Cyst wall |
| 117 | G12D | R201C | 76 | M | unknown | IPMN | high | 5.0 | not determined | gastric | head | Cyst wall |
| 118 | G12D | No mutation detected | 73 | F | Yes | IPMN | high | 2.8 | branch | gastric | head | Cyst wall |
| 119 | G12R | R201H | 71 | F | No | IPMN | low | 4.0 | branch | gastric | body/tail | Cyst wall |
| 120 | G12V | R201H | 72 | M | No | IPMN | high | 7.0 | main | intestinal | body/tail | Cyst wall |
| 121 | No mutation detected | R201H | 77 | M | No | IPMN | high | 7.0 | main | intestinal | entire pancreas | Cyst wall |
| 122 | G12V | R201H | 35 | F | No | IPMN | high | 8.0 | main | intestinal | head | Cyst wall |
| 123 | G12V | R201H | 69 | M | No | IPMN | high | 5.1 | mixed | intestinal | head | Cyst wall |
| 124 | G12V | No mutation detected | 64 | F | Yes | IPMN | low | 2.0 | branch | gastric | body/tail | Cyst wall |
| 125 | No mutation detected | R201C | 76 | F | Yes | IPMN | high | 1.5 | main | intestinal | body/tail | Cyst wall |
| 126 | G12D | No mutation detected | 69 | F | unknown | IPMN | intermediate | 3.4 | mixed | gastric | body/tail | Cyst wall |
| 127 | G12R | R201H | 73 | F | unknown | IPMN | high | 14 | main | not determined | entire pancreas | Cyst wall |
| 128 | G12D | No mutation detected | 74 | M | unknown | IPMN | intermediate | 8.0 | main | gastric | head | Cyst wall |
| 129 | G12D | No mutation detected | 56 | M | unknown | IPMN | intermediate | 4 | branch | gastric | head | Cyst wall |
| 130 | G12D & G12V | R201C | 68 | F | Yes | IPMN | intermediate | 2.5 | branch | gastric | body/tail | Cyst fluid |
| 131 | G12V | R201C | 73 | F | Yes | IPMN | high | 6.0 | mixed | intestinal | entire pancreas | Cyst fluid |
| 132 | G12V & G12R | R201H | 71 | M | No | IPMN | intermediate | 3.0 | mixed | gastric | body/tail | Cyst wall |

FIG. 6C

Table S3. Characteristics of patients with cyst types other than IPMN, including GNAS and KRAS mutation status.

| Cyst # | KRAS | GNAS | Age at surgery | Sex | History of smoking | Post-operative diagnosis | Cyst Grade | Cyst diameter (cm) | Cyst location | Sample type |
|---|---|---|---|---|---|---|---|---|---|---|
| OT01 | No mutation detected | No mutation detected | 57 | F | unknown | SCA | NA | 2.5 | head | Cyst fluid |
| OT02 | No mutation detected | No mutation detected | 58 | F | No | SCA | NA | 1.5 | Neck | Cyst fluid |
| OT03 | No mutation detected | No mutation detected | 54 | M | unknown | SCA | NA | 2 | head | Cyst fluid |
| OT04 | No mutation detected | No mutation detected | 57 | M | Yes | SCA | NA | 2 | body/tail | Cyst fluid |
| OT05 | No mutation detected | No mutation detected | 69 | F | unknown | SCA | NA | 3 | tail | Cyst fluid |
| OT06 | No mutation detected | No mutation detected | 57 | F | Yes | SCA | NA | 3 | body/tail | Cyst fluid |
| OT07 | No mutation detected | No mutation detected | 59 | F | No | SCA | NA | 3 | head | Cyst fluid |
| OT08 | No mutation detected | No mutation detected | 64 | F | No | SCA | NA | 3 | head | Cyst fluid |
| OT09 | No mutation detected | No mutation detected | 60 | F | unknown | SCA | NA | 3.1 | head | Cyst fluid |
| OT10 | No mutation detected | No mutation detected | 56 | M | Yes | SCA | NA | 4 | body | Cyst fluid |
| OT11 | No mutation detected | No mutation detected | 47 | F | Yes | SCA | NA | 4 | head | Cyst fluid |
| OT12 | No mutation detected | No mutation detected | 49 | F | unknown | SCA | NA | 4 | head | Cyst fluid |
| OT13 | No mutation detected | No mutation detected | 52 | M | unknown | SCA | NA | 4.5 | tail | Cyst fluid |
| OT14 | No mutation detected | No mutation detected | 58 | F | unknown | SCA | NA | 4.8 | tail | Cyst fluid |
| OT15 | No mutation detected | No mutation detected | 46 | M | Yes | SCA | NA | 5 | head | Cyst fluid |
| OT16 | No mutation detected | No mutation detected | 81 | F | unknown | SCA | NA | 5 | head | Cyst fluid |
| OT17 | No mutation detected | No mutation detected | 77 | F | unknown | SCA | NA | 6 | body | Cyst fluid |
| OT18 | No mutation detected | No mutation detected | 61 | F | unknown | SCA | NA | 6 | tail | Cyst fluid |
| OT19 | No mutation detected | No mutation detected | 72 | M | Yes | SCA | NA | 7 | body/tail | Cyst fluid |
| OT20 | No mutation detected | No mutation detected | 61 | F | unknown | SCA | NA | 7.5 | body | Cyst fluid |
| OT21 | No mutation detected | No mutation detected | 77 | F | Yes | SCA | NA | 8 | body/tail | Cyst fluid |
| OT22 | No mutation detected | No mutation detected | 55 | F | unknown | SCA | NA | 10 | tail | Cyst fluid |
| OT23 | No mutation detected | No mutation detected | 61 | F | unknown | SCA | NA | 13 | tail | Cyst fluid |
| OT24 | No mutation detected | No mutation detected | 45 | M | No | SCA | NA | 1.5 | head | Cyst fluid |
| OT25 | No mutation detected | No mutation detected | 63 | M | unknown | SCA | NA | 1.8 | body/tail | Cyst fluid |
| OT26 | No mutation detected | No mutation detected | 62 | F | No | SCA | NA | 10.5 | body/tail | Cyst fluid |
| OT27 | No mutation detected | No mutation detected | 57 | F | No | SCA | NA | 2.5 | body/tail | Cyst fluid |
| OT28 | No mutation detected | No mutation detected | 86 | F | No | SCA | NA | 2.5 | body/tail | Cyst fluid |
| OT29 | No mutation detected | No mutation detected | 58 | M | Yes | SCA | NA | 2.5 | body/tail | Cyst fluid |
| OT30 | No mutation detected | No mutation detected | 66 | F | unknown | SCA | NA | 2.6 | head | Cyst fluid |
| OT31 | No mutation detected | No mutation detected | 72 | F | unknown | SCA | NA | 2.8 | body/tail | Cyst fluid |
| OT32 | No mutation detected | No mutation detected | 63 | F | Yes | SCA | NA | 3 | body/tail | Cyst fluid |
| OT33 | No mutation detected | No mutation detected | 47 | F | Yes | SCA | NA | 3 | head | Cyst fluid |
| OT34 | No mutation detected | No mutation detected | 64 | M | Yes | SCA | NA | 3.5 | head | Cyst fluid |
| OT35 | No mutation detected | No mutation detected | 52 | F | No | SCA | NA | 3.5 | body/tail | Cyst fluid |
| OT36 | No mutation detected | No mutation detected | 71 | F | Yes | SCA | NA | 3.7 | body/tail | Cyst fluid |
| OT37 | No mutation detected | No mutation detected | 77 | F | Yes | SCA | NA | 4 | body/tail | Cyst fluid |
| OT38 | No mutation detected | No mutation detected | 36 | F | unknown | SCA | NA | 4.1 | head | Cyst fluid |

FIG. 7A

| ID | Mutation | Mutation | Age | Sex | Symptoms | Type | Grade | Size | Location | Sample |
|---|---|---|---|---|---|---|---|---|---|---|
| OT39 | No mutation detected | No mutation detected | 74 | F | unknown | SCA | NA | 4.5 | head | Cyst fluid |
| OT40 | No mutation detected | No mutation detected | 66 | F | No | SCA | NA | 5 | body/tail | Cyst fluid |
| OT41 | No mutation detected | No mutation detected | 40 | F | unknown | SCA | NA | 5.4 | body/tail | Cyst fluid |
| OT42 | No mutation detected | No mutation detected | 56 | F | No | SCA | NA | 5.9 | body/tail | Cyst fluid |
| OT43 | No mutation detected | No mutation detected | 19 | F | unknown | SCA | NA | 6.6 | head | Cyst fluid |
| OT44 | No mutation detected | No mutation detected | 69 | M | unknown | SCA | NA | 7.5 | head | Cyst fluid |
| OT45 | No mutation detected | No mutation detected | 32 | F | Yes | MCN | Not determined | 2.3 | body | Cyst fluid |
| OT46 | No mutation detected | No mutation detected | 51 | F | Yes | MCN | Not determined | 2.5 | body | Cyst fluid |
| OT47 | G12V | No mutation detected | 65 | F | No | MCN | Not determined | 2.5 | tail | Cyst fluid |
| OT48 | G12V | No mutation detected | 46 | F | No | MCN | low | 2.5 | tail | Cyst fluid |
| OT49 | G12V | No mutation detected | 43 | F | Yes | MCN | Not determined | 3.2 | body | Cyst fluid |
| OT50 | No mutation detected | No mutation detected | 46 | F | No | MCN | Not determined | 3.5 | body | Cyst fluid |
| OT51 | No mutation detected | No mutation detected | 65 | F | Yes | MCN | Not determined | 4 | tail | Cyst fluid |
| OT52 | No mutation detected | No mutation detected | 60 | F | Yes | MCN | low | 4 | body/tail | Cyst fluid |
| OT53 | No mutation detected | No mutation detected | 58 | F | No | MCN | Not determined | 4.5 | tail | Cyst fluid |
| OT54 | No mutation detected | No mutation detected | 52 | F | No | MCN | Not determined | 5 | body / tail | Cyst fluid |
| OT55 | No mutation detected | No mutation detected | 24 | F | unknown | MCN | low | 5 | body/tail | Cyst fluid |
| OT56 | No mutation detected | No mutation detected | 43 | F | Yes | MCN | Not determined | 5.5 | body | Cyst fluid |
| OT57 | No mutation detected | No mutation detected | 59 | F | Yes | MCN | low | 7 | body/tail | Cyst fluid |
| OT58 | G12V | No mutation detected | 42 | F | No | MCN | Not determined | 8.5 | body / tail | Cyst fluid |
| OT59 | No mutation detected | No mutation detected | 34 | F | unknown | MCN | low | 16 | head | Cyst fluid |
| OT60 | No mutation detected | No mutation detected | 57 | F | No | MCN | low | 17 | body | Cyst fluid |
| OT61 | G12D | No mutation detected | 66 | F | Yes | MCN | low | 1.5 | head | Cyst fluid |
| OT62 | G12R | No mutation detected | 39 | F | unknown | MCN | low | 2.5 | body/tail | Cyst fluid |
| OT63 | No mutation detected | No mutation detected | 36 | F | unknown | MCN | low | 3.5 | head | Cyst fluid |
| OT64 | No mutation detected | No mutation detected | 54 | F | unknown | MCN | low | 5.5 | body/tail | Cyst fluid |
| OT65 | G12D | No mutation detected | 42 | F | unknown | MCN | intermediate | 7.4 | head | Cyst fluid |
| OT66 | No mutation detected | No mutation detected | 45 | F | unknown | IOPN | high | 3.1 | head | Cyst fluid |
| OT67 | No mutation detected | No mutation detected | 36 | M | No | IOPN | high | 4.5 | head | Cyst fluid |
| OT68 | No mutation detected | No mutation detected | 72 | M | Yes | IOPN | high | 6.0 | head | Cyst fluid |
| OT69 | No mutation detected | No mutation detected | 74 | M | Yes | IOPN | high | 6.0 | body/tail | Cyst fluid |
| OT70 | No mutation detected | No mutation detected | 55 | F | unknown | IOPN | high | 10.0 | tail | Cyst fluid |

FIG. 7B

Fig. 8
Table S4. Quantification of mutations in selected IPMNs containing both *GNAS* and *KRAS* mutations.

| IPMN # | KRAS mutant allele(s) | Major KRAS mutant allele | Major KRAS allele freq | Major KRAS allele fraction/total mutant alleles* |
|---|---|---|---|---|
| 31 | G12D & G12V & G12R | G12D | 29% | 97% |
| 36 | G12D | G12D | 18% | Not applicable |
| 41 | G12D | G12D | 3.0% | NA |
| 42 | G12D | G12D | 17% | NA |
| 43 | G12D | G12D | 33% | NA |
| 48 | G12R | G12S | 1.6% | NA |
| 57 | G12R | G12S | 0.8% | NA |
| 65 | G12D & G12R | G12D | 27% | 88% |
| 67 | G12V | G12V | 8.0% | NA |
| 72 | G12D | G12D | 36% | NA |
| 78 | G12D & G12V | G12V | 0.9% | 65% |
| 79 | G12V & G12R | G12V | 11% | 60% |
| 86 | G12D & G12V | G12V | 18% | 50% |
| 87 | G12D & G12V & G12R | G12V | 8% | 46% |
| 100 | G12R | G12S | 1.4% | NA |
| 105 | G12V | G12V | 1.0% | NA |
| 130 | G12D & G12V | G12V | 4.0% | 56% |

* NA = Not applicable because there was only a single mutation identified in the IPMN.

Fig. 9

Table S5. Comparison of mutational status in DNA from IPMNs and pancreatic adenocarcinomas from the same patients.

| IPMN # | Lesion | *KRAS* mutation | *GNAS* mutation |
|---|---|---|---|
| 9 | IPMN | G12V & G12D | R201H & R201C |
| | Cancer | G12V | R201H |
| 11 | IPMN | No mutation detected | R201C |
| | Cancer | No mutation detected | R201C |
| 20 | IPMN | G12V | R201C |
| | Cancer | G12V | R201C |
| 33 | IPMN | G12V | R201H |
| | Cancer | G12R | No mutation detected |
| 122 | IPMN | G12V | R201H |
| | Cancer | G12V | R201H |
| 125 | IPMN | No mutation detected | R201C |
| | Cancer | No mutation detected | R201C |
| 127 | IPMN | G12D | R201H |
| | Cancer | G12D | R201H |
| 131 | IPMN | G12V | R201C |
| | Cancer | G12V | R201C |

Fig. 10

Table S6. Oligonucleotide primer and probe sequences.

| Gene | Used for: | 5'-Modification | Mutation | Sequence (5'-3')* |
|---|---|---|---|---|
| PCR Amplification Primers | | | | |
| GNAS | GNAS Forward Primer | None | GNAS 201 R201C, R201H | GGCTTTGGTGAGATCCATTG |
| GNAS | GNAS Reverse Primer | None | GNAS 201 R201C, R201H | TCCACCTGGAACTTGGTCTC |
| KRAS | PCR forward primer | None | KRAS G12D, G12R, G12V | GATCATATTCGTCCAGAAATGATTC |
| KRAS | PCR Reverse Primer | None | KRAS G12D, G12R, G12V | TGACTGAATATAAACTTGTGGTAGTTG |
| Ligation probes | | | | |
| GNAS | WT-specific probe | 6-FAM | R201H | ATG GAG AAC TTG ACG TCC TG TTC GCT GCC G |
| GNAS | Mutant-specific probe | HEX | R201H | TTCGCTGCCA |
| GNAS | Common anchoring probe | Phosphate | R201H | TGT CCT GAC TTC GG TGT TCA CTA GTC ATG CTT |
| GNAS | WT-specific probe | 6-FAM | R201C | ATG GAG AAC TTG ACG TCC AC CTT CGC TGC C |
| GNAS | Mutant-specific probe | HEX | R201C | CTT *CGC T*G*C T |
| GNAS | Common anchoring probe | Phosphate | R201C | GTG TCC TGA CTT GG TGT CCA CTA GTC ATG CTT |
| GNAS | WT-specific probe | 6-FAM | G12D | ATG GAG AAC TTG ACG TCC T C CTA CGC CAC |
| GNAS | Mutant-specific probe | HEX | G12D | TGGCT*ACGC*C*AT |
| GNAS | Common anchoring probe | Phosphate | G12D | CAG CTC CAA CTA GG TGT CCA CTA GTC ATG CTT |
| KRAS | WT-specific probe | 6-FAM | G12R | TCC CGC GAA ATT AAT ACG AG CTT CGC CACC |
| KRAS | Mutant-specific probe | HEX | G12R | CTA CGC CAC G |
| KRAS | Common anchoring probe | Phosphate | G12R | AGC TCC AAC TAC GG TGT CCA CTA GTC ATG CTT |
| KRAS | WT-specific probe | 6-FAM | G12V | ATG GAG AAC TTG ACG TCC T C CTA CGC CAC |
| KRAS | Mutant-specific probe | HEX | G12V | CCT ACG CCA A |
| KRAS | Common anchoring probe | Phosphate | G12V | CAG CTC CAA CTA GG TGT CCA CTA GTC ATG CTT |
| BEAMing probes | | | | |
| GNAS | Detecting beads containing either WT or mutant sequences | ROX | R201C | CTGAAACAAAATTGAAGGT |
| GNAS | WT-specific probe | Cy3 | R201C | AGGACACgGGCAGCGA |
| GNAS | Mutant-specific probe | Cy5 | R201C | AGGACACaGGCAGCGA |
| GNAS | Detecting beads containing either WT or mutant sequences | ROX | R201H | CTGAAACAAAATTGAAGGT |
| GNAS | WT-specific probe | Cy3 | R201H | CAGGACACGGGCAGCG |
| GNAS | Mutant-specific probe | Cy5 | R201H | CAGGACACATGGCAGCG |
| KRAS | Detecting beads containing either WT or mutant sequences | ROX | G12D | TGACGATACAGCTAATTCA |
| KRAS | WT-specific probe | Cy3 | G12D | GGAGCTGGTGGCGTA |
| KRAS | Mutant-specific probe | Cy5 | G12D | GGAGCTGATGGCGTA |
| KRAS | Detecting beads containing either WT or mutant sequences | ROX | G12V | TGACGATACAGCTAATTCA |
| KRAS | WT-specific probe | Cy3 | G12V | GGAGCTGGTGGCGTA |
| KRAS | Mutant-specific probe | Cy5 | G12V | GGAGCTGTTGGCGTA |
| KRAS | Detecting beads containing either WT or mutant sequences | ROX | G12R | TGACGATACAGCTAATTCA |
| KRAS | WT-specific probe | Cy3 | G12R | TGGAGCTGGTGCGT |
| KRAS | Mutant-specific probe | Cy5 | G12R | TGGAGCTCGTGGCGT |

* indicates LNA linkages; red font indicates additional nucleotides used to discriminate WT from Mutant sequences in the ligation assays.

ENRICHMENT OF NUCLEIC ACIDS BY COMPLIMENTARY CAPTURE

This invention was made with funds from the United States government. The United States retains certain rights to the invention according to the terms of CA 43460, CA 57345, and CA 62924.

TECHNICAL FIELD OF THE INVENTION

This invention is related to the area of genetic markers. In particular, it relates to methods for enriching nucleic acid sequences for analyses. The nucleic acid sequences may comprise genetic markers, such as cancer or other disease markers.

SUMMARY OF THE INVENTION

According to one aspect of the invention a sample comprising nucleic acids is enriched for target nucleic acid analytes. A set of probes for one or more analytes of interest is synthesized. The probes are complementary to plus or minus strands of a target nucleic acid analyte. Each probe has a common 5' and 3' universal priming site. The set of probes is amplified using primers complementary to the universal priming sites. The amplified probes are ligated to each other to form concatamers. The concatamers are isothermally amplified. The amplified concatamers are bound to a solid support. The solid support is contacted with the sample comprising nucleic acids under hybridization conditions so that complementary nucleic acids in the sample are captured on the solid support and non-complementary nucleic acids are removed. Captured nucleic acids are eluted from the solid support.

According to another aspect of the invention a sample is enriched for target nucleic acid analytes. A set of probes for one or more analytes of interest is synthesized. The probes are complementary to plus or minus strands of a target nucleic acid analyte. Each probe has a common 5' and 3' universal priming site. The set of probes is amplified using primers complementary to the universal priming sites. The amplified probes are ligated together to form concatamers. The concatamers are isothermally amplified in the presence of biotyinylated nucleotides, such that biotinylated nucleotides are incorporated into the concatamers. The amplified concatamers are contacted with the sample nucleic acids to form a mixture. The mixture is subjected to hybridization conditions so that complementary nucleic acids in the mixture hybridize to the concatamers. The mixture is contacted with a solid support which comprises avidin or streptavidin, so that hybridized nucleic acids are captured on the solid support. The solid support is washed to remove nucleic acids which do not comprise biotin. The captured nucleic acids are eluted from the solid support.

These and other embodiments which will be apparent to those of skill in the art upon reading the specification provide the art with methods for assessing, characterizing, and detecting genetic markers, such as cancer markers, and in particular pancreatic cancer markers. In particular, it provides methods for enriching for desired analytes.

BRIEF DESCRIPTION OF THE DRAWINGS

(FIG. 2A) Schematic of the ligation assay. Oligonucleotide probes complementary to either the WT or mutant sequences were incubated with a PCR product containing the sequence of interest. The WT- and mutant-specific probes were labeled with the fluorescent dyes 6-FAM and HEX, respectively, and the WT-specific probe was 11 bases longer than the mutant-specific probe. After ligation to a common anchoring primer, the ligation products were separated on a denaturing polyacrylamide slab gel. Further details of the assay are provided in the Materials and Methods. (FIG. 2B) Examples of the results obtained with the ligation assay in the indicated patients. Templates were derived from DNA of normal duodenum or IPMN tissue. Each lane represents the results of ligation of one of four independent PCR products, each containing 200 template molecules. The probe in the left panel was specific to the GNAS R201H mutation and the probe on the right panel was specific for the GNAS R201C mutation.

(FIG. 4A) H&E-stained section of a formalin-fixed, paraffin embedded sample (shows two apparently independent IPMNs with distinct morphologies located close to one another. The IPMN of gastric epithelial subtype (black arrow) harbored a GNAS R201C and a KRAS G12'V while the IPMN showing the intestinal subtype (red arrow) contained a GNAS R201C mutation but no KRAS mutation. (FIG. 4B) H&E stained section of a different, typical IPMN (FIG. 4C) Same IPMN as in FIG. 4B after microdissection of the cyst wall.

FIGS. 5A-5D. (Table S1.) Genes analyzed by massively parallel sequencing in IPMN cyst fluids.

FIGS. 6A-6C. (Table S2.) Characteristics of patients with IPMNs analyzed in this study, including GNAS and KRAS mutation status.

FIGS. 7A-7B. (Table S3.) Characteristics of patients with cyst types other than IPMN, including GNAS and KRAS mutation status.

FIG. 8. (Table S4.) Quantification of mutations in selected IPMNs containing both GNAS and KRAS mutations.

FIG. 9. (Table S5.) Comparison of mutational status in DNA from IPMNs and pancreatic adenocarcinomas from the same patients.

FIG. 10. (Table S6.) Oligonucleotide primer and probe sequences (SEQ ID NO: 4-38).

DETAILED DESCRIPTION OF THE INVENTION

Figure 1:
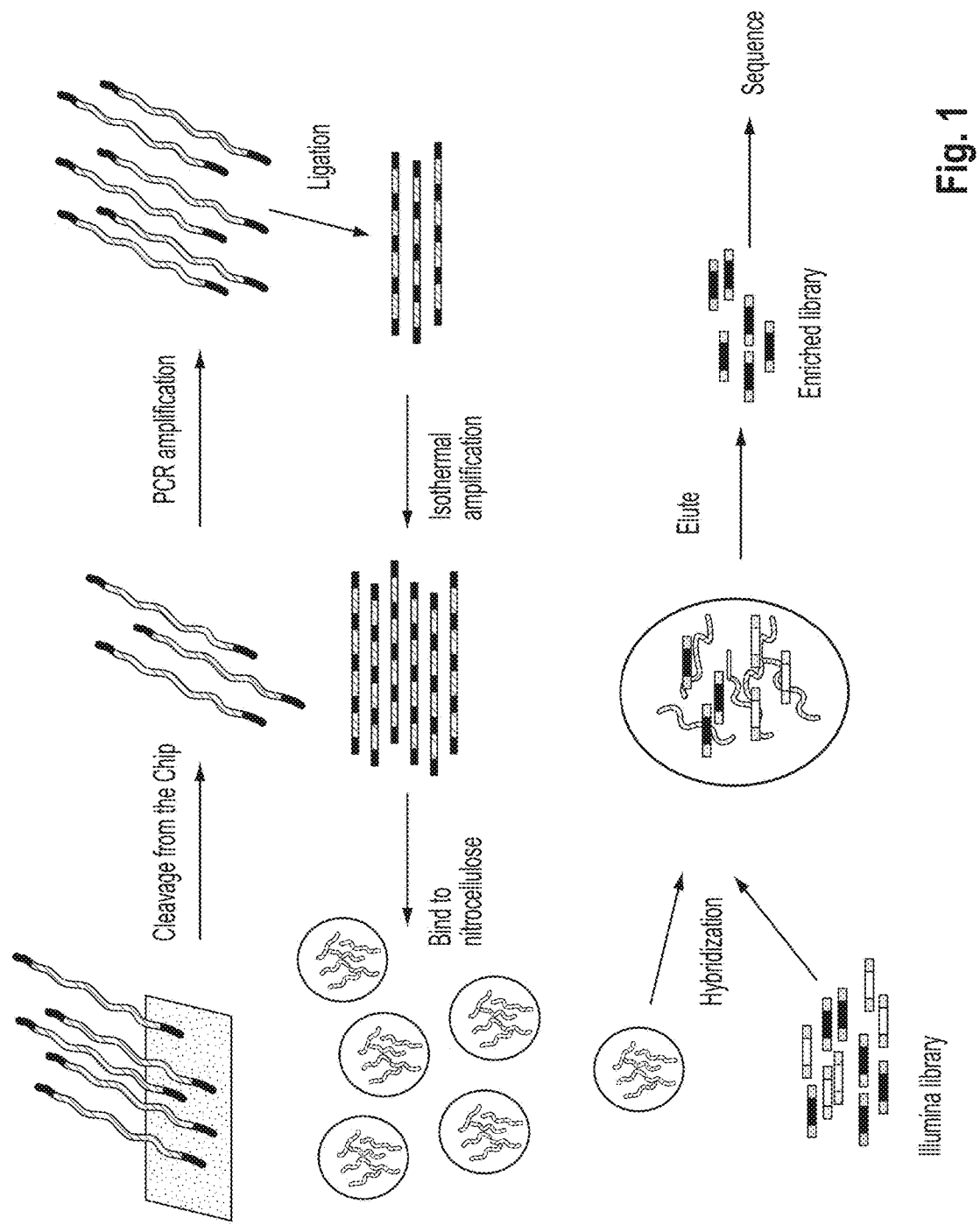
FIG. 1 provides a schematic of a capture strategy. Overlapping oligonucleotides flanked by universal sequences complimentary to the 169 genes listed in FIGS. 5A-D (Table S1) were synthesized on an array. The oligonucleotides were cleaved off the array, amplified by PCR with universal primers, ligated into concatamers and amplified in an isothermal reaction. They were then bound to nitrocellulose filters and used as bait for capturing the desired fragments. An Illumina library was constructed from the sample DNA. The library was denatured and hybridized to the probes immobilized on nitrocellulose. The captured fragments were eluted, PCR amplified and sequenced on an Illumina GAIIX instrument.

Capturing and amplifying analyte nucleic acids from dilute samples can be particularly taxing. Enrichment for desired sequences can make assays feasible that would otherwise fall below detection limits. Test samples can be from any appropriate source in the patient's body that will have nucleic acids from a cancer or lesion that can be collected and tested. In some cases the nucleic acids will be amplified prior to testing. Suitable test samples may be obtained from pancreatic cyst fluid, pancreatic cyst wall tissue, pancreatic ductal adenocarcinoma tissue, blood, stool, saliva, sputum, bronchoalveolar lavage, urine, and pancreatic juice. The samples may be collected using any means conventional in the art, including from surgical samples, from biopsy samples, from endoscopic ultrasound (EUS), phlebotomy, etc. Obtaining the samples may be performed by the same person or a different person that conducts the subsequent analysis. Samples may be stored and/or transferred after collection and before analysis. Samples may be fractionated, treated, purified, enriched, prior to assay.

Solid supports which may be used are any which are convenient for the particular purpose and situation. These may be filters, beads, magnetic beads, plastic surfaces, microtiter plates, resins, etc. The supports can be treated and derivatized as is known in the art. In particular assays, attachment of a specific binding pair member may be used. For example, avidin or streptavidin may be used as one binding pair member, and biotin as another. One binding pair member may be used on the nucleic acid analyte and one binding pair member may be on the solid support. As exemplified below, biotin can be incorporated into a nucleic acid analyte using biotinylated dNTPs during amplification or synthesis. Other binding pairs which provide a strong bond may be used as well.

Isothermal amplification is one means for producing large amounts of particular sequences. Isothermal amplification is also known as Multiple Displacement Amplification or rolling circle amplification. Other means as are known can also be used.

Ligation reactions are used to join together individual oligonucleotide probes into long polymers or concatamers. Ligation reaction conditions and enzymes for performing these reactions are known in the art and can be used as is convenient.

Any means of testing for a mutation, including without limitation, a point mutation, a deletion, an amplification, a loss of heterozygosity, a rearrangement, a duplication, may be used. As an example, a mutation in codon 201 of GNAS or codon 12 of KRAS may be assayed. Any means of testing for a mutation may be used. Mutations may be detected by sequencing, by hybridization assay, by ligation assay, etc. If locations of the relevant mutations are defined, specific assays which focus on the identified locations may be used. Identifying a mutation as somatic can be accomplished by comparing a test sample to a non-neoplastic sample, either from the same patient or from a healthy individual. The defined locations of some mutations permit focused assays limited to an exon, domain, or codon. But non-targeted assays may also be used, where the location of a mutation is unknown. Any assay that is performed on a test sample involves a transformation, for example, a chemical or physical change or act. Assays and determinations are not performed merely by a perceptual or cognitive process in the body of a person.

Probes and/or primers may contain the wild-type or a mutant sequence. These can be used in a variety of different assays, as will be convenient for the particular situation. Selection of assays may be based on cost, facilities, equipment, electricity availability, speed, reproducibility, compatibility with other assays, invasiveness of sample collection, sample preparation, etc.

Any of the assay results may be recorded or communicated, as a positive act or step. Communication of an assay result, diagnosis, identification, or prognosis, may be, for example, orally between two people, in writing, whether on paper or digital media, by audio recording, into a medical chart or record, to a second health professional, or to a patient. The results and/or conclusions and/or recommendations based on the results may be in a natural language or in a machine or other code. Typically such records are kept in a confidential manner to protect the private information of the patient.

Collections of probes, primers, control samples, and reagents can be assembled into a kit for use in the methods. The reagents can be packaged with instructions, or directions to an address or phone number from which to obtain instructions. An electronic storage medium may be included in the kit, whether for instructional purposes or for recordation of results, or as means for controlling assays and data collection.

Control samples can be obtained from the same patient from a tissue that is not apparently diseased. Alternatively, control samples can be obtained from a healthy individual or a population of apparently healthy individuals. Control samples may be from the same type of tissue or from a different type of tissue than the test sample.

The data described below document the existence of a heretofore unappreciated molecular pathway leading to pancreatic neoplasia. There is no doubt that GNAS mutations plays a driving role in this IPMN-specific pathway: the mutations are remarkably common and they occur at a single codon (201), mutations of which are known to endow cells with extremely high adenyl cyclase activity and cAMP levels (37-39). Based on their rate of mutation and specificity (30), the probability that these mutations are passengers rather than drivers of IPMN development is negligible.

Figure 4:
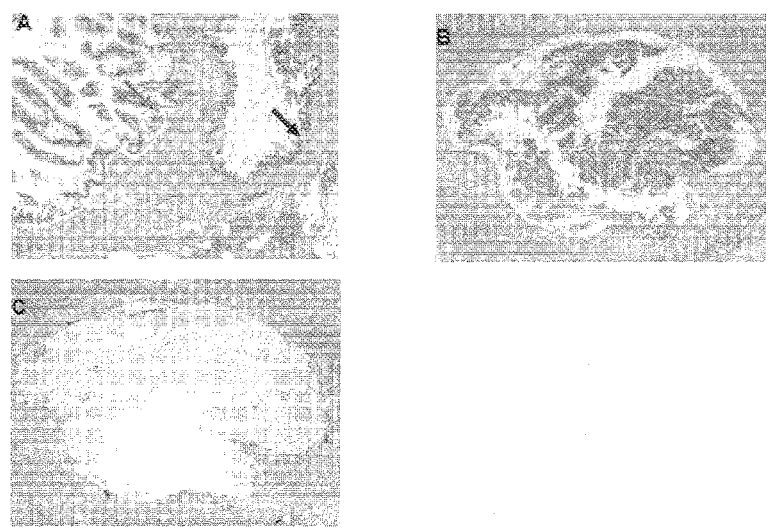
FIGS. 4A-4C show IPMN morphologies.

The data also demonstrated that >96% of IPMNs have either a GNAS or KRAS (v-Ki-ras2 Kirsten rat sarcoma viral oncogene homolog) mutation and more than half have both mutations. Which mutation—KRAS or GNAS—arises first? There were 20 cases in which GNAS mutations were identified in the absence of KRAS mutations and six additional cases in which GNAS mutations were at least 5 times more abundant than KRAS mutations in the same cyst fluid (FIG. 8 (Table S4)). The converse situation—KRAS mutations in the absence of GNAS mutations—was also observed in many cases (FIG. 6 (Table S2)). These data, in combination with the demonstration that more than one KRAS or more than one GNAS mutation could be identified in the same cyst (FIG. 8 (Table S4)), suggests two models for IPMN development. First, it is possible that IPMN locules represent independent entities whose evolution is unrelated to other locules within the same IPMN. This model is inconsistent with our data because two adjacent locules within a single grossly distinct IPMN were more likely to contain the same KRAS or GNAS mutation than the lining epithelium from two topographically different cysts, as noted in the Results section. Second, it is possible that all IPMNs are initiated by a single founding mutation in either GNAS or in KRAS. Subsequent mutations of cells within the cystic lesion would lead to independent clonal expansions, perhaps represented by different locules. Such polyclonality has been observed in colorectal adenomas, which are initiated by mutations in APC pathway genes but sometimes progress through heterogeneous KRAS mutations to a transient polyclonal stage (40). This stage is eventually replaced by subsequent clonal expansion of a cell with one of these KRAS mutations (40). A related possibility is that IPMNs are initiated by a genetic or epigenetic alteration in a gene other than KRAS or GNAS, and that we have observed subsequent clonal expansions of these initiated cells. Finally, it is possible that most IPMNs are indeed initiated by a mutation (in GNAS, KRAS, or another gene), but that occasionally two such IPMNs, initiated by completely different cells, develop adjacent to one another. This appeared to be the situation for the case shown in FIG. 4A, for example. Though these models are difficult to distinguish from one another, it is possible that lineage tracking can be accomplished by complete sequencing of IPMN locule genomes in the future (41).

Apart from its implications for understanding IPMN development, our data have potentially important practical ramifications. The appropriate management of a patient with a pancreatic cyst depends on the type of cyst (42). In particular, it is generally agreed that there is no need to remove asymptomatic SCAs because these lesions have a vanishingly small malignant potential (43). However, the distinction between SCA and mucinous cystic lesions (IPMN and MCN) of the pancreas is often not easy, even after extensive imaging and follow-up (6). One example of these difficulties is provided by the nature of the lesions in our study: the great majority of the 44 SCAs we examined were removed because they were preoperatively believed to be cysts with malignant potential. Hence, many of these 44 surgical procedures were likely unnecessary.

These diagnostic difficulties have long been appreciated and have spurred attempts to develop biomarkers as adjuncts to clinical data, imaging, and cytology (44). Indeed, new protein and glycoprotein markers are showing promising results (45, 46). One conceptual disadvantage of these protein biomarkers is that they are simply associated with cyst development and do not play a pathogenic role. Alterations of oncogenes such as KRAS are attractive alternatives because they are intimately involved in pathogenesis (47-50). In the largest previous study to date on such alterations, 45% of the fluids from mucinous cysts were shown to contain KRAS mutations (25). Our data demonstrates that KRAS mutations are actually present in a larger fraction of IPMNs, probably a result of the more sensitive methods used in our study combined with optimization of procedures used to purify cyst fluid DNA (see Materials and Methods). Third, and most important, the combination of GNAS and KRAS mutation detection provides high sensitivity and specificity for distinguishing between SCAs and IPMNs. The vast majority of IPMNs had a GNAS and/or a KRAS (95% CI 91% to 99%) while no SCAs had either mutation. These data indicate a sensitivity of 0.96 (95% CI 0.91 to 0.99) and a specificity of 1.0 (97.5% one-sided CI 0.92 to 1) for distinguishing between these two lesions. In addition, although not as sensitive, the presence of a GNAS mutation in cyst fluid can also distinguish IPMNs from MCNs (FIG. 7 (Table S3)). The assay involves just two amplicons (GNAS and KRAS) and can be performed with as little as 250 ul of cyst fluid.

Several caveats to the potential utility of such tests should be noted. First, the analysis of cyst fluid obtained through EUS, though safe, is an invasive procedure. Complications include bleeding, infection, and pancreatitis, are reversible, and are generally observed in <1% of patients (reviewed in (51)). Second, neither KRAS nor GNAS mutations can distinguish high grade or invasive from low grade IPMNs. The supplementation of KRAS and GNAS mutational analyses with other markers indicative of grade would clearly be useful (11). Third, we cannot yet reliably distinguish IPMNs from MCNs through the analysis of cyst fluid. Although MCNs do not contain GNAS mutations, a third of them contain KRAS mutations (FIG. 7 (Table S3)) MCN-specific mutations may be identified in the future through a strategy similar to the one we used to identify mutations in IPMNs.

Astute clinicians and pathologists have long suspected that adenocarcinomas of the pancreas arising in IPMNs are a "different disease" than those arising locally distant or in the absence of an IPMN (15, 52). We here provide evidence in support of this hypothesis and identify a key molecular component that underlies this difference.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

Materials and Methods
Patients and Specimens

The present study was approved by the Institutional Review Boards of Johns Hopkins Medical Institutions, Memorial Sloan Kettering Cancer Center and the University of Indiana. We included individuals in whom pancreatic cyst fluid samples from pancreatectomy specimens and/or fresh frozen tumor tissues were available for molecular analysis. Relevant demographic, clinicopathologic data were obtained from prospectively maintained clinical databases and correlated with mutational status.

Pancreatic cyst fluids were harvested in the Surgical Pathology suite from surgically resected pancreatectomy specimens with a sterile syringe. Aspirated fluids were stored at −80° C. within 30 min of resection. Fresh-frozen tissue specimens of surgically resected cystic neoplasms of the pancreas were obtained through a prospectively maintained Johns Hopkins Surgical Pathology Tumor Bank. These lesions as well as normal tissues were macrodissected using serial frozen sections to guide the trimming of OCT embedded tissue blocks to obtain a minimum neoplastic cellularity of 80%. Formalin-fixed and paraffin-embedded archival tissues from surgically resected pancreata were sectioned at 6 μm, stained with hematoxylin and eosin, and dissected with a sterile needle on a SMZ1500 stereomicroscope (Nikon). An estimated 5,000-10,000 cells were microdissected from each lesion. Lesions were classified as IPMNs, MCNs, or SCAs using standard criteria (53). IPMNs were subtyped by internationally accepted criteria (54).

DNA Purification

DNA was purified from frozen cyst walls using an AllPrep kit (Qiagen) and from formalin-fixed, paraffin-embedded sections using the QIAamp DNA FFPE tissue kit (Qiagen) according to the manufacturer's instructions. DNA was purified from 250 μL of cyst fluid by adding 3 ml RLTM buffer (Qiagen) and then binding to an AllPrep DNA column (Qiagen) following the manufacturer's protocol. DNA was quantified in all cases with qPCR, employing primers and conditions as described (55).

Illumina Library Preparation

Cyst fluid DNA was first quantified through real-time PCR using primers specific for repeated sequences in DNA (LINE) as described (56). A minimum of 100 ng DNA from cyst fluid was used to make Illumina libraries according to manufacturer's protocol with the exception that the amount of adapters was decreased in proportional fashion when a lower amount of template DNA was used. The number of PCR cycles used to amplify the library after ligation of adapters was varied to ensure a yield of ~5 ug of the final library product for capture.

Target DNA Enrichment

The targeted region included all of the 3386 exons of 169 cancer related genes and was enriched with custom-made oligonucleotide probes. The design of each oligonucleotide was as follows: 5'-TCCCGCGACGAC-36 bases from the genomic region of interest -GCTGGAGTCGCG-3' (SEQ ID NO: 1). Probes were designed to capture both the plus and the minus strand of the DNA and had a 33-base overlap. The probes were custom-synthesized on a chip. The oligonucleotides were cleaved from the chip by treatment for five hours with 3 ml 35% ammonium hydroxide at room temperate. The solution was transferred to two 2-ml tubes, dried under vacuum, and re-dissolved in 400 ul RNase and DNase free water. Five ul of the solution were used for PCR amplification with primers complementary to the 12 base sequence common to all probes: 5-TGATCCCGCGACGA*C-3' (SEQ ID NO: 2), 5'-GACCGCGACTCCAG*C-3' (SEQ ID NO: 3), with * indicating a phosphorothioate bond. The PCR mix contained 27 ul $H_2O$, 5 ul template DNA, 2 ul forward primer (25 uM), 2 ul reverse primer (25 uM), 4 ul $MgCl_2$ (50 mM), 5 ul 10× Platinum Taq buffer (Life Technologies), 4 ul dNTPs (10 mM each) and 1 ul Platinum Taq (5 U/ul, Life Technologies). The cycling conditions were: one cycle of 98° C. for 30 s; 35 cycles of 98° C. for 30 s, 40° C. for 30 s, 60° C. for 15 s, 72° C. for 45 s; one cycle of 72° C. for 5 min. The PCR product was purified using a MinElute Purification Column (Qiagen) and end-repaired using End-IT DNA End-Repair Kit (Epicentre) as follows: 34 ul DNA, 5 ul 10× End-Repair Buffer, 5 ul dNTP Mix, 5 ul ATP, 1 ul End-Repair Enzyme Mix. The mix was incubated at room temperature for 45 minutes, and then purified using a MinElute Purification Column (Qiagen). The PCR products were ligated to form concatamers using the following protocol: 35 ul End-Repaired DNA product, 40 ul 2×T4 DNA ligase buffer, 5 ul T4 DNA ligase (3000 units; Enzymatics Inc.) The mix was incubated at room temperature for 4 hours, then purified using QiaQuick Purification Column (Qiagen), and quantified by absorption at 260 nm.

Replicates of 50 ng of concatenated PCR product were amplified in 25 ul solution using the REPLI-g midi whole genome amplification kit (Qiagen) according to the manufacturer's protocol. The RepliG-amplified DNA (20 ug) was then bound to a nitrocellulose membrane and used to capture DNA libraries as described (57). In general, 5 ug of library DNA were used per capture. After washing, the captured libraries were ethanol precipitated and redissolved in 20 ul TE buffer. The DNA was then amplified in a PCR mix containing 51 ul $dH_2O$, 20 ul 5× Phusion buffer, 5 ul DMSO, 2 ul 10 mM dNTPs, 50 pmol Illumina forward and reverse primers, and 1 ul Hotstart Phusion enzyme (New England Biolabs) using the following cycling program: 98° C. for 30 sec; 15 cycles of 98° C. for 25 sec., 65° C. for 30 sec, 72° C. for 30 sec; and 72° C. for 5 min. The amplified PCR product was purified using a NucleoSpin column (Macherey Nagel, inc.) according to the manufacturer's suggested protocol except that the NT buffer was not diluted and the DNA bound to the column was eluted in 35 ul elution buffer. The captured library was quantified with realtime PCR with the primers used for grafting to the Illumina sequencing chip.

Ligation Assay

PCR products containing codon 12 of KRAS and codon 201 of GNAS were amplified using the primers described in FIG. 10 (Table S6). Each 10-ul PCR contained 200 template molecules in 5 ul of 2× Phusion Flash PCR Master Mix (New England Biolabs) and final concentrations of 0.25 uM forward and 1.5 uM reverse primers. Note that the mutant-specific probes sometimes included locked nucleic acid residues (FIG. 10 (Table S6); Exiqon). The following cycling conditions were used: 98° C. for 2 min; 3 cycles of 98° C. for 10 sec., 69° C. for 15 sec, 72° C. for 15 sec; 3 cycles of 98° C. for 10 sec., 66° C. for 15 sec, 72° C. for 15 sec; 3 cycles of 98° C. for 10 sec., 63° C. for 15 sec, 72° C. for 15 sec; 41 cycles of 98° C. for 10 sec., 60° C. for 60 sec. Reactions were performed in at least quadruplicate and each was evaluated independently. Five ul of a solution containing 0.5 ul of Proteinase K, (18.8 mg/ml, Roche) and 4.5 ul of $dH_2O$ was added to each well and incubated at 60° C. for 30 minutes to inactivate the Phusion polymerase and then for 10 min at 98° C. to inactivate the Proteinase K.

The ligation assay was based on techniques described previously, using thermotolerant DNA ligases (58-61). Each 10-ul reaction contained 2-ul of PCR product (unpurified), 1 ul of 10× Ampligase buffer (Epicentre), 0.5 ul of Ampligase (5 U/ul, Epicentre), anchoring primer (final concentration 2 uM), WT-specific primer (final concentration 0.1 uM), and mutant-specific primer (final concentration 0.025 uM). The sequences of these primers are listed in FIG. 10 (Table S6). The following cycling conditions were used: 95° C. for 3 min; 35 cycles of 95° C. for 10 sec., 37° C. for 30 sec, 45° C. for 60 sec. Five ul of each reaction was added to 5 ul of formamide and the ligation products separated on a 10% Urea-Tris-Borate-EDTA gel (Invitrogen) and imaged with an Amersham-GE Typhoon instrument (GE Healthcare).

BEAMing Assays

These were performed as described (62) using the PCR products generated for the ligation assay as templates and the oligonucleotides listed in FIG. 10 (Table S6) as hybridization probes.

Statistical Analysis

Fisher's exact tests were used to compare the differences between proportions and Wilcoxon Rank Sum tests were used to compare differences in mutational status by age. Confidence intervals for the prevalence of mutations were estimated using the binomial distribution. To compare the prevalence of mutations in grossly distinct IPMNs to adjacent locules within a single grossly distinct IPMN, we compared the probability of observing given KRAS or GNAS mutation in the 111 distinct IPMNs to conditional probability that given the first locule sequenced contained a specific KRAS or GNAS mutation all other locules contained the same KRAS or GNAS mutations. The probabilities of GNAS or KRAS mutations occurring by chance was calculated using a binomial distribution and the previously estimated mutation rates of tumors or normal cells (30). STATA version 11 was used for all statistical analysis (63).

EXAMPLE 2

Massively Parallel Sequencing of 169 Genes in Cyst Fluid DNA

To initiate this study, we determined the sequences of 169 presumptive cancer genes in the cyst fluids of 19 IPMNs, each obtained from a different patient. Thirty-three of the 169 were oncogenes and the remainder were tumor suppressor genes. Though only a tiny subset of these 169 genes were known to be mutated in PDAs, all were known to be frequently mutated in at least one solid tumor type (FIG. 5 (Table S1)). We additionally sequenced these genes in normal pancreatic, splenic or intestinal tissues of the same patients to determine which of the alterations identified were somatic. We chose to use massively parallel sequencing rather than Sanger sequencing for this analysis because we did not know what fraction of DNA purified from the cyst fluid was derived from neoplastic cells. Massively parallel sequencing has the capacity to identify mutations present in 2% or more of the studied cells while Sanger sequencing often requires >25% neoplastic cells for this purpose. IPMNs are by definition connected with the pancreatic duct system and the cyst fluid containing cellular debris and shed DNA from the neoplastic cells can be expected to be admixed with that of the cells and secretions derived from normal ductal epithelial cells.

We devised a strategy to capture sequences of the 169 genes from cyst fluid DNA (FIG. 1). In brief, 244,000 oligonucleotides, each 60 bp in length and in aggregate covering the exonic sequences of all 169 genes, were synthesized in parallel using phosphoramadite chemistry on a single chip synthesized by Agilent Technologies. After removal from the chip, the oligonucleotide sequences were amplified by PCR and ligated together. Multiple displacement amplification was then used to further amplify the oligonucleotides, which were then bound to a filter. Finally, the filter was used to capture complementary DNA sequences from the cyst fluids and corresponding normal samples, and the captured DNA was subjected to massively parallel sequencing.

The target region corresponding to the coding exons of the 169 genes encompassed 584,871 bp. These bases were redundantly sequenced, with 902±411 (mean±1 SD) fold-coverage in the 38 samples sequenced (19 IPMN cyst fluids plus 19 matched DNA samples from normal tissues of the same patients). This coverage allowed us to confidently detect somatic mutations present in >5% of the template molecules.

There were only two genes mutated in more than one IPMN—KRAS, which was mutated in 14 of the 19 IPMNs, and GNAS, which was mutated in 6 IPMNs. The mutations in GNAS all occurred at codon 201, resulting in either a R201H or R201C substitution. GNAS is a well-known oncogene that is mutated in pituitary and other uncommon tumor types (16-19). However, such mutations have rarely been reported in common epithelial tumors (20-22). In pituitary tumors, mutations cluster at two positions—codons 201 and 227 (16, 19). This clustering provides extraordinary opportunities for diagnosis, similar to that of KRAS. For example, the clustering of KRAS mutations has facilitated the design of assays to detect mutations in tumors of colorectal cancer patients eligible for therapy with antibodies to EGFR (23). All twelve KRAS mutations identified through massively parallel sequencing of cyst fluids were at codon 12, resulting in a G12D, G12V, or G12R amino acid change. KRAS mutations at codon 12 have previously been identified in the vast majority of PDAs as well as in 40 to 60% of IPMNs (24-29). GNAS mutations have not previously been identified in pancreatic cysts or in PDAs.

EXAMPLE 3

Frequency of KRAS and GNAS Mutations in Pancreatic Cyst Fluid DNA

We next determined the frequency of KRAS codon 12 and GNAS codon 201 mutations in a larger set of IPMNs. The clinical characteristics of all IPMNs analyzed in this study are listed in FIG. 6 (Table S2). To ensure that the analyses were performed robustly, we carried out preliminary experiments with cyst fluids from patients with known mutations based on the massively parallel sequencing experiments described above. We tested several methods for purifying DNA from often viscous cyst fluids and used the optimum method for subsequent experiments. Quantitative PCR was used to determine the number of amplifiable template molecules recovered with this procedure. In eight cases, we compared pelleted cells to supernatants derived from the same cyst fluid samples and found that the fraction of mutant templates in both compartments was similar. On the basis of these results, we purified DNA from 0.25 ml of whole cyst fluid (cells plus supernatant) and, as assessed by quantitative PCR, recovered an average of 670±790 ng of usable DNA.

Figure 2A:
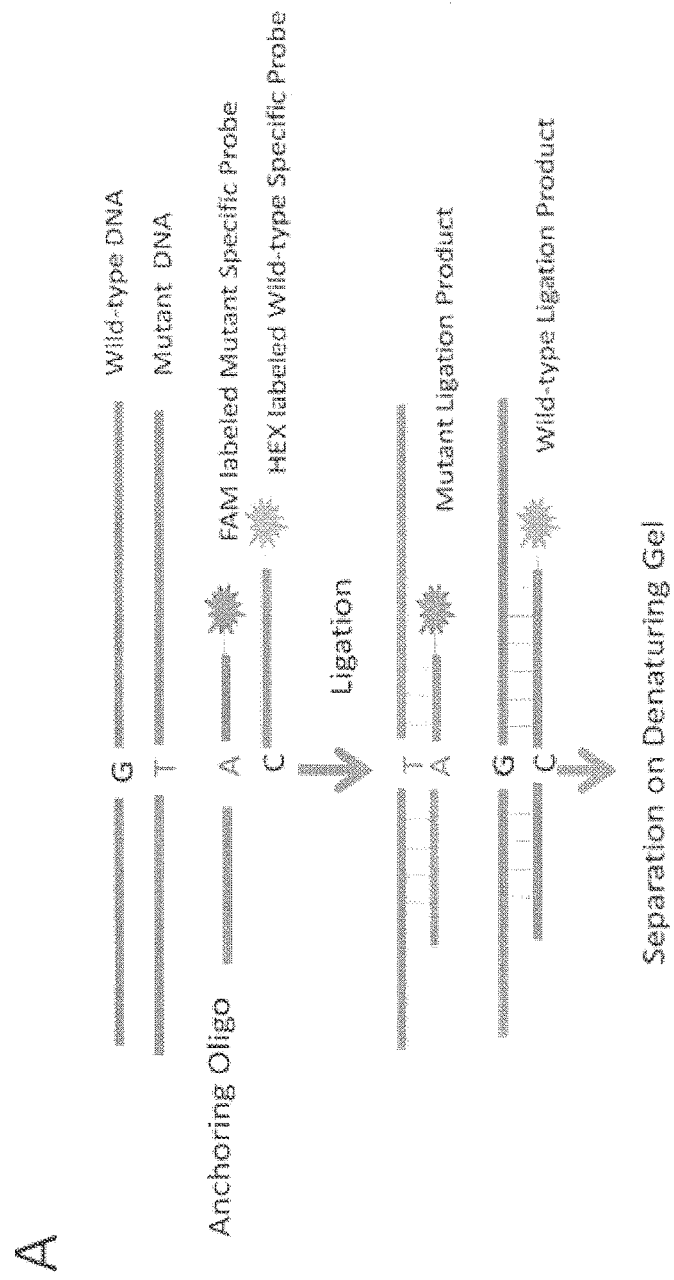
FIGS. 2A-2B show a ligation assays used to assess KRAS (v-Ki-ras2 Kirsten rat sarcoma viral oncogene homolog) and GNAS (guanine nucleotide binding protein (G protein), alpha stimulating activity polypeptide 1) mutations.
Figure 2B:
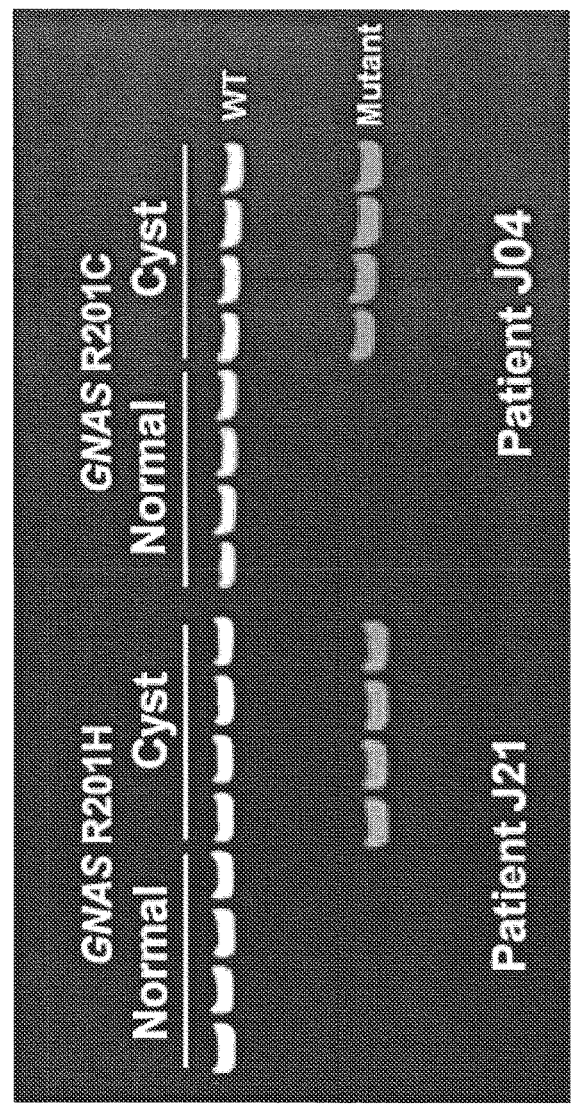

For each of 84 cyst fluid samples (an independent cohort of 65 patients plus the 19 patients whose fluids had been studied by massively parallel sequencing), we analyzed ~800 template molecules for five distinct mutations, three at KRAS codon 12 and two within GNAS codon 201 (see Materials and Methods). A PCR/ligation method that had the capacity to detect one mutant template molecule among 200 normal (wild-type, WT) templates was used for these analyses (FIG. 2A). We identified GNAS and KRAS mutations in 61% and 82% of the IPMN fluids, respectively (representative examples in FIG. 2B). In those samples without GNAS codon 201 mutations, we searched for GNAS codon 227 mutations, but did not find any. We also analyzed macro- and microdissected frozen or paraffin-embedded cyst walls from an independent collection of 48 surgically resected IPMNs, and similarly identified a high prevalence of GNAS (75%) and KRAS (79%) mutations. In aggregate, 66% of 132 IPMNs harbored a GNAS mutation, 81% harbored a KRAS mutation, slightly more than half (51%) harbored both GNAS and KRAS mutations, while at least one of the two genes was mutated in 96.2% (FIG. 6 (Table S2)). Given background mutation rates in tumors or normal tissues (30), the probability that either GNAS or KRAS mutations occurred by chance alone was less than $10^{-30}$. There were no significant correlations between the prevalence of KRAS or GNAS mutations and age, sex, or smoking history of the patients (P>0.05) (Table 1). Small (<3 cm) as well as larger cysts had similar fractions of both KRAS and GNAS mutations and the location of the IPMN (head, body, or tail) did not correlate with the presence of mutation in either gene (Table 1). GNAS and KRAS mutations were present in low-grade as well as in high-grade IPMNs. The prevalence of KRAS mutations was higher in lower grade lesions (P=0.03) whereas the prevalence of GNAS mutations was somewhat higher in more advanced lesions (P=0.11) (Table 1). GNAS, as well as KRAS mutations were present in each of the three major histologic types of IPMNs—intestinal, pancreatobiliary, and gastric. However, the prevalence of the mutations varied across the histological types (P<0.01 for both KRAS and GNAS). GNAS mutations were most prevalent in the intestinal subtype (100%), KRAS mutations had the highest frequency (100%) in the pancreatobiliary subtype and had the lowest frequency (42%) in the intestinal subtype (Table 1).

We then determined whether GNAS mutations were present in SCAs, a common but benign type of pancreatic cystic neoplasm. We examined a total of 44 surgically resected SCAs, each from a different patient (42 cyst fluids and 2 cyst walls). Many of these cysts were surgically resected because they clinically mimicked an IPMN. They would have likely not been surgically excised had they been known to be SCAs. The SCAs averaged 5.0±2.8 cm in maximum diameter (FIG. 7 (Table S3)) similar to the IPMNs (4.4±3.7 maximum diameter, FIG. 6 (Table S2)). There was little difference in the locations of the SCAs and IPMNs within the pancreas (FIGS. 6 and 7 (Tables S2 and S3)). However, no GNAS or KRAS mutations were identified in the SCAs, in marked contrast to the IPMNs (p<0.001, Fisher's Exact Test). GNAS mutations were also not identified in any of 21 MCNs (p=0.005 when compared to IPMNs, Fisher's Exact Test), although KRAS mutations were found in 33% of MCNs (FIG. 7 (Table S3)). GNAS mutations were also not identified in five examples of an uncommon type of cyst, called intraductal oncocytic papillary neoplasm (IOPN), with characteristic oncocytic features (FIG. 7 (Table S3)).

Figure 3:
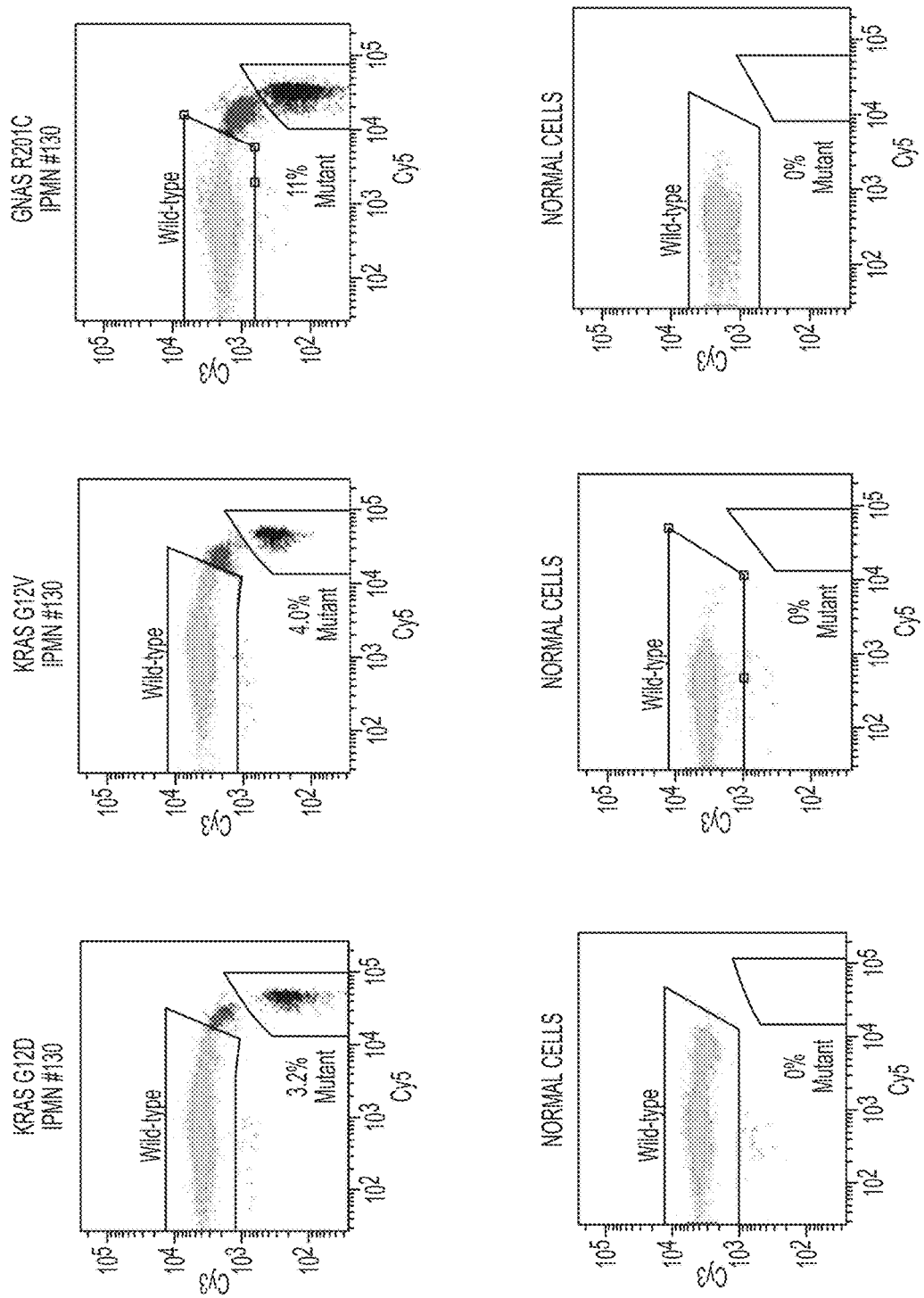
FIG. 3 shows BEAMing assays used to quantify mutant representation. PCR was used to amplify KRAS or GNAS sequences containing the region of interest (KRAS codon 12 and GNAS codon 201). The PCR-products were then used as templates for BEAMing, in which each template was converted to a bead containing thousands of identical copies of the templates (34). After hybridization to Cy3- or Cy5-labeled oligonucleotide probes specific for the indicated WT or mutant sequences, respectively, the beads were analyzed by flow cytometry. Scatter plots are shown for templates derived from the DNA of IPMN 130 or from normal spleen. Beads containing the WT or mutant sequences are widely separated in the scatter plots, and the fraction of mutant-containing beads are indicated. Beads whose fluorescence spectra lie between the WT and mutant-containing beads result from inclusion of both WT and mutant templates in the aqueous nanocompartments of the emulsion PCR.

We investigated clonality in more detail by precisely quantifying the levels of mutations in the subset of cyst fluids containing more than one mutation of the same gene. To accomplish this, we used a technique called BEAMing (34). Through this method, individual template molecules are converted into individual magnetic beads attached to thousands of molecules with the identical sequence. The beads are then hybridized with mutation-specific probes and analyzed by flow cytometry (FIG. 3). The analysis of 17 IPMN cyst fluids, each with mutations in both KRAS and GNAS, showed that the fraction of mutant alleles varied widely, ranging from 0.8% to 45% of the templates analyzed. There was an average of 12.8%±12.2% mutant alleles of KRAS and an average of 24.4±13.1% mutant alleles of GNAS in the 17 IPMN cyst fluids examined (FIG. 8 (Table S4)). In two of the seven IPMNs with more than one KRAS mutation, there was a predominant mutant that out-numbered the second KRAS mutant by >5:1 (FIG. 8 (Table S4)). Similarly, two of the four cases harboring two different GNAS mutations had a predominant mutant (FIG. 8 (Table S4)). In the other cases, the different mutations in KRAS (or GNAS) were distributed more evenly (FIG. 8 (Table S4)). These data support the idea that cells within a subset of IPMNs had undergone independent clonal expansions, giving rise to apparent polyclonality (35).

TABLE 1

Correlations between mutations and clinical and histopathologic parameters of IPMNs

|  |  | N, total | KRAS mutation N | KRAS mutation % | P-value | GNAS mutation N | GNAS mutation % | P-value |
|---|---|---|---|---|---|---|---|---|
| Age in years | <65 years | 29 | 22 | 75.9 | 0.42 | 18 | 62.1 | 0.62 |
|  | ≥65 years | 103 | 85 | 82.5 |  | 69 | 67 |  |
| Gender | Male | 70 | 58 | 82.9 | 0.58 | 51 | 72.9 | 0.07 |
|  | Female | 62 | 49 | 79 |  | 36 | 58.1 |  |
| History of smoking | Yes | 25 | 21 | 84 | 0.77 | 17 | 68 | 0.85 |
|  | No | 37 | 30 | 81.1 |  | 26 | 70.3 |  |
| Grade | Low | 23 | 20 | 87 | 0.43 | 11 | 47.8 | 0.04 |
|  | Intermediate | 51 | 46 | 90.2 | (low vs. | 34 | 66.7 | (low vs. |
|  | High | 58 | 41 | 70.7 | others) | 42 | 72.4 | others) |
| Duct type | Main | 35 | 23 | 65.7 | 0.002 | 24 | 68.6 | 0.37 |
|  | Branch | 64 | 58 | 90.6 | (main vs. | 38 | 59.4 | (main vs. |
|  | Mixed | 28 | 21 | 75 | branch) | 20 | 71.4 | branch) |
| Subtype | Gastric | 52 | 45 | 86.5 | 0.02 | 34 | 65.4 | 0.002 |
|  | Pancreatobiliary | 7 | 7 | 100 | (panc. vs | 3 | 42.9 | (panc. vs |
|  | Intestinal | 13 | 6 | 46.2 | intestinal) | 13 | 100 | intestinal) |
| Diameter | <3 cm | 62 | 49 | 79 | 0.58 | 41 | 66.1 | 0.96 |
|  | ≥3 cm | 70 | 58 | 82.9 |  | 46 | 65.7 |  |
| Location | Proximal (head) | 77 | 64 | 83.1 | 0.44 | 53 | 68.8 | 0.38 |
|  | Distal (body, tail) | 49 | 38 | 77.6 | (prox. vs | 30 | 61.2 | (prox. vs |
|  | Proximal and distal | 6 | 5 | 83.3 | distal) | 4 | 66.7 | distal) |
| Associated cancer | Yes | 24 | 18 | 75 | 0.4 | 18 | 75 | 0.3 |
|  | No | 108 | 89 | 82.4 |  | 69 | 63.9 |  |

EXAMPLE 4

IPMN Polyclonality

Figure 6B:
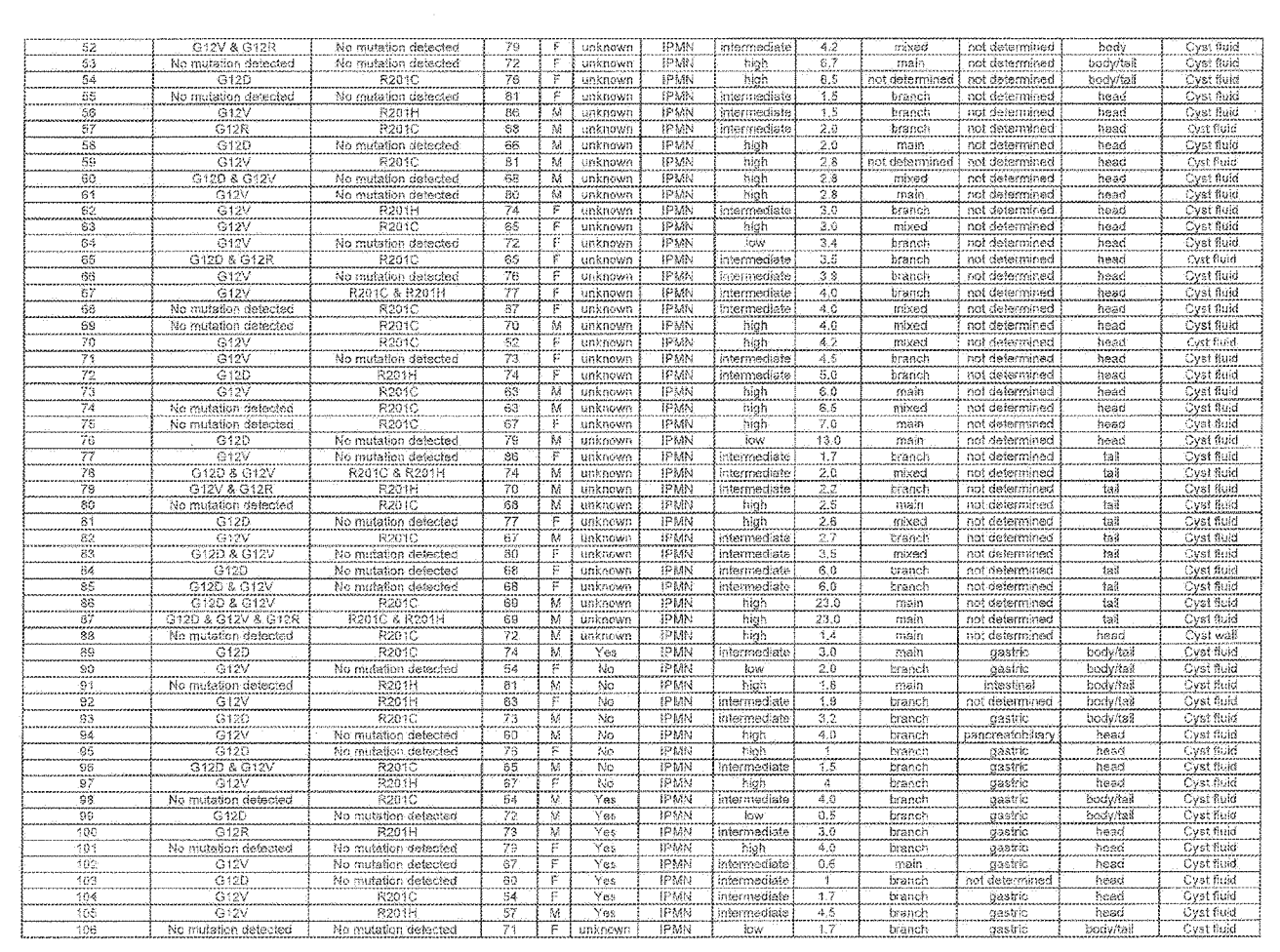

KRAS G12D, G12V, and G12R mutations were found in 43%, 39%, and 13% of IPMNs, respectively (FIG. 6 (Table S2)). A small fraction (11%) of the IPMNs contained two different KRAS mutations and 2% contained three different mutations. Likewise, GNAS R201C and GNAS R201H mutations were present in 39% and 32% of the IPMNs, respectively, and 4% of the IPMNs had both mutations (FIG. 6 (Table S2)). More than one mutation in KRAS in IPMNs has been observed in prior studies of IPMNs (31-33) and the multiple KRAS and GNAS mutations are suggestive of a polyclonal origin of the tumor.

IPMNs are often multilocular or multifocal in nature, looking much like a bunch of grapes (FIG. 4A) (36). To determine the relationship between cyst locules (individual grapes) and cyst fluid, we microdissected the walls from individual locules of each of ten IPMNs from whom cyst fluid was available (example in FIGS. 4B and C). The individual locule walls generally appeared to be monoclonal, as more than one KRAS mutation was only found in one (4.5%) of the 22 locules examined. No locule wall contained more than one GNAS mutation and two adjacent locules within a single grossly distinct IPMN were more likely to contain the same KRAS or GNAS mutation than the lining epithelium from two topographically different IPMNs (p<0.05, Fisher's Exact Test for KRAS G12D, KRAS G12R and GNAS R201H mutations; P<0.10 for KRAS G12V and GNAS R201H mutations). All of the ten KRAS and six GNAS mutations identified in the cyst fluid could be identified in the corresponding locule walls. These data leave little doubt that the mutations in the cyst fluid are derived from the cyst locule walls and indicate that the cyst fluid provides an excellent representation of the neoplastic cells in an IPMN.

EXAMPLE 5

GNAS Mutations in Invasive Cancers Associated with IPMNs

Prior whole exome sequencing had not revealed any GNAS mutations in 24 typical PDA that occurred in the absence of an associated IPMN (29). We extended these data by examining 95 additional surgically resected PDAs in pancreata without evidence of IPMNs for mutations in GNAS R201H or R201C, using the ligation assay described above. Again, no GNAS mutations were identified in PDAs arising in the absence of IPMNs.

We suspected that IPMNs containing GNAS mutations had the potential to progress to an invasive carcinoma because fluids from IPMNs with high-grade dysplasia contained such mutations (Table 1). However, in light of the multilocular and multifocal nature of IPMNs described above, it was not clear whether the cells of the locule(s) that progress to an invasive carcinoma were those that contained GNAS mutations. To address this question, we purified DNA from invasive pancreatic adenocarcinomas that developed in association with IPMNs. In each case, the neoplastic cells of the IPMN and of the invasive adenocarcinoma were carefully microdissected. In seven of the eight patients, the identical GNAS mutation found in the neoplastic cells of the IPMN was found in the concurrent invasive adenocarcinoma (FIG. 9 (Table S5)). The KRAS mutational status of the PDA was consistent with that of the associated IPMN in the same seven cases. In the eighth case, the KRAS and GNAS mutations identified in the neoplastic cells of the IPMN were not found in the associated PDA, suggesting that this invasive cancer arose from a separate precursor lesion (FIG. 9 (Table S5)). Though KRAS mutations were found commonly in both types of PDAs, there was a dramatic difference between the prevalence of GNAS mutations in PDAs associated with IPMNs (7 of 8) vs. that in PDAs unassociated with IPMNs (0 of 116; p<0.001, Fisher's Exact Test).

EXAMPLE 6

A Protocol for Enrichment on Beads
Cleave Oligos from the Chip
Place the chip into the corner of a Micro-Seal bag (Model 50068, DAZEY corporation) cut to ~10.5×5.5 cm.
Seal the unsealed two sides so that the bag ends up 8 cm×2.6 cm, tightly wrapping the chip.
While in the Seal-a-Meal bag, treat for five hours with 3 ml 28% ammonium hydroxide at room temperate by rotator (360 deg rotation). (Make sure the chip is fully immersed in the solution)
Transfer the solution into two 2-ml eppendorf tubes, and speed vacuum dried at temperate 50° C. (normally it will take 5-8 hours)
(For speed vacuum, turn on the cooler one hour before you use the vacuum)
Re-dissolve the oligos in a combined 400 ul RNase and DNase free water.

Amplify the Oligos
Make 3×50 ul PCR mix for each chip, the PCR mix contains the following:
X ul H2O
1 ul (well 1), 2 ul (well 2), 5 ul (well 3)
2 ul forward primer (25 uM): 5'-TGATCCCGCGACGA*C-3', where * indicates phosphorothioate
2 ul reverse primer (25 uM): 5'-GACCGCGACTCCAG*C-3', where * indicates phosphorothioate
4 ul MgCl2 (50 mM)
5 ul 10× Platinum Taq buffer (Life Technologies)
4 ul dNTPs (10 mM each)
1 ul Platinum Taq (5 U/ul, Life Technologies) (Titanium and Phusion both did not work).
Note: Because of the alkalic condition after cleavage, the more template you add, the less PCR product you get.
The cycling conditions were: 1×98° C. for 30 s
35 cycles of 98° C. for 30 s, 40° C. for 30 s, 60° C. for 15 s, 72° C. for 45 s
one cycle of 72° C. for 5 min
Run the gel to see a smear from 60 bp to 120 bp. 120 bp product may be dimers, which won't interfere with capture.
The PCR products were combined, and add 2 ul Sodium Acetate (3M, pH 5.2) purified using a MinElute Purification Column (Qiagen), elute twice in 65° C. pre-warmed buffer with 17 ul each (total of 34 ul).
End-Repair the PCR Product
End-repair using End-IT DNA End-Repair Kit (Epicentre) as follows:
34 ul DNA
5 ul 10× End-Repair Buffer
5 ul dNTP Mix
5 ul ATP
1 ul End-Repair Enzyme Mix
Incubate at room temperature for 45 minutes,
Purified using a MinElute Purification Column (Qiagen), elute twice in 65° C. pre-warmed buffer with 17.5 ul each (total of 35 ul).
Ligate the PCR Product
The PCR products were ligated to form concatamers using the following protocol:
35 ul End-Repaired DNA product
40 ul 2×T4 DNA ligase buffer (Enzymatics Inc.)
5 ul T4 DNA ligase (600 units/ul; Enzymatics Inc.)
The mix was incubated at room temperature for at least 4 hours, (you can leave it overnight.)
The product was purified using QiaQuick PCR Purification Column (Qiagen) (not MinElute), elute twice in 65° C. pre-warmed buffer with 25 ul each (total of 50 ul).
Quantify by absorption at 260 nm. (Normally you get around 3 ug DNA product.)
Dilute the product to 20 ng/ul using TE buffer.
Isothermal Amplification of the Probe with Bio-dUTP [RepliG-Midi Kit (not Mini Kit), Qiagen]

TABLE 1

| Preparation of Buffer D1 (Volumes given are suitable for up to 15 reactions) | |
| --- | --- |
| Component | Volume |
| Reconstituted Buffer DLB | 9 μl |
| Nuclease-free water | 32 μl |
| Total volume | 41 μl |

TABLE 2

Preparation of Buffer N1 (Volumes given are suitable for up to 15 reactions)

| Component | Volume |
|---|---|
| Stop solution | 12 μl |
| Nuclease-free water | 68 μl |
| Total volume | 80 μl |

Place 2.5 μl template DNA into a microcentrifuge tube.
Add 2.5 μl Buffer D1 to the DNA. Mix by vortexing and centrifuge briefly
Incubate the samples at room temperature (15-25° C.) for 3 min.
Add 5 μl Buffer N1 to the samples. Mix by vortexing and centrifuge briefly.
Prepare a master mix on ice according to Table 3 (see below). Mix and centrifuge briefly.
Important: Add the master mix components in the order listed in Table 3. After addition of water and REPLI-g Midi Reaction Buffer,
briefly vortex and centrifuge the mixture before addition of REPLI-g Midi DNA Polymerase. The master mix should be kept on ice and used
immediately upon addition of the REPLI-g Midi DNA Polymerase.

TABLE 3

Preparation of Master Mix

| Component | Volume/reaction |
|---|---|
| REPLI-g Midi Reaction Buffer | 14.5 μl |
| Biotin-dUTP(1 mM) (Cat. No.11093070910, Roche Applied Science) | 2.5 ul |
| REPLI-g Midi DNA Polymerase | 0.5 μl |
| Total volume | 17.5 μl |

Add 17.5 μl of the master mix to 10 μl denatured DNA that was neutralized with N1 as described above. Transfer the mix to the PCR plate.
Incubate at 30° C. for 16 h in PCR machine.
Inactivate REPLI-g Midi DNA Polymerase by heating the sample at 65° C. for 3 min.
Transfer the mix using 2×120 ul TE to a 1.5 ml tube.
Incubate the tube in 100° C. heating block for 20 minutes.
Purify the product using two QiaQuick PCR Purification Columns (Qiagen) (not MinElute), i.e., use 2 columns for one 27.5 ul reaction.
Elute each column twice with 65° C. pre-warmed buffer with 27.5 ul, for a total of 55 ul, so there will be 110 ul of eluate from the two columns which should be pooled.
Quantify by absorption at 260 nm using nanodrop (I know it's single-strand DNA now, but I still use ds-DNA calculations in nanodrop)
In general, you will get ~180-210 ng/ul. If it's too off, there must be something wrong.
DNA Capture
A mix was prepared as follows:
4 ug DNA library (20 ul, 200 ng/ul)
7 ul Human cot-1 DNA (Cat. No. 15279011, Invitrogen)
3 ul Herring Sperm DNA (Cat. No. 15634-017, Invitrogen)
10 ul Blocking Oligos, 1 nmol/ul each.

Block Oligo 1:

AATGATACGGCGACCACCGAGATCTACACTCTTTCCCTACACGACGCTCT

Block Oligo 2:

CAAGCAGAAGACGGCATACGAGATCGGTCTCGGCATTCCTGCTGAACCGC 5 ul Capture Probe (~200 ng/ul)
The mix is heated at 95° C. for 7 min, and 65° C. for 2 min (use only one compress pad in PCR machine)
Add 25 ul of the 65° C. prewarmed 2.8× hybridization buffer (final conc of hyb buffer will then be 1×)
2.8× hybridization buffer: (14×SSPE, 14×Denhardt's, 14 mM EDTA, 0.28% SDS), using the following reagents:
20×SSPE: (0810-4L, AMRESCO)
Denhardt's Solution, 50×, 50 ml (70468, usb)
EDTA: 0.5M, PH 8.0 (46-034-CI, Mediatech Inc.)
(In case the DNA library cone is <200 ng/ul, then still use 4 ug DNA and 7 ul Cot-1, 3 ul Herring sperm, etc. but use proportionally larger volumes of 2.8× HybBuffer
Incubate at 65 deg for 22 hours for hybridization with PCR machine lid heat on.
Washing Procedure
Wash 50 ul MyOne beads (Invitrogen) 3 times in 1.5 ml tule and resuspend in 60 μl 1× binding buffer (1M NaCl, 10 mM Tris-HCl, pH 7.5, and 1 mM EDTA.)
Add equal volume (70 ul) of 2× binding buffer (2 M NaCl, 20 mM Tris-HCl, pH 7.5, and 2 mM EDTA.) to hybrid mix, and transfer to tube with beads. Total Volume should be 200 ul.
Vortex the mix thoroughly. And rotate 360 deg. for 1 hour at Room Temperature.
After binding, the beads are pulled down, and washed 15 minutes at RT in 0.5 ml Wash Buffer 1 (1×SSC/0.1% SDS)
Wash the beads for 15 minutes at 65° C. on a heating block with shaking, five times in 0.5 ml Wash Buffer 3 (0.1×SSC and 0.1% SDS)
Hybrid-selected DNA are resuspended in 50 μl 0.1 M NaOH at RT for 10 min.
The beads are pulled down, the supernatant transferred to a tube containing 70 μl Neutralizing Buffer (1 M Tris-HCl, pH 7.5)
Neutralized DNA is desalted and concentrated on a QIAquick MinElute column and eluted in 20 μl.
Note: Wash Buffer 2 (5.2 M Betaine, 0.1×SSC and 0.1% SDS) is a more stringent wash buffer.
For more stringent wash, you can substitute the first WB3 wash with WB2, then continue with four washes with WB3.
Change the post-Capture amplification Cycle number to 16 cycles if you use a more stringent wash.
Post-Capture Amplification
PCR mix containing:
20 captured DNA
51 ul dH2O
20 ul 5× Phusion buffer
5 ul DMSO
2 ul 10 mM dNTPs
0.5 ul (50 pmol) Illumina forward primer (QC1 primer for barcoding)
0.5 ul (50 pmol) Illumina reverse primer (Barcoding reverse primers for barcoding)
1 ul Hotstart Phusion enzyme (New England Biolabs)
The cycling conditions were: 1×98° C. for 30 s 14 cycles of 98° C. for 25 s, 65° C. for 30 s, 72° C. for 30 s one cycle of 72° C. for 5 min The PCR is done in two wells for each sample, 50 ul each (no oil on top).

The amplified PCR product was purified using a NucleoSpin column (Macherey Nagel, inc.), eluted twice in 65° C. pre-warmed buffer with 17.5 ul (total of 35 ul).

Use NanoDrop to quantify yield, which should be ~20 ng/ul.

REFERENCES

The disclosure of each reference cited is expressly incorporated herein.

1. T. A. Laffan, K. M. Horton, A. P. Klein, B. Berlanstein, S. S. Siegelman, S. Kawamoto, P. T. Johnson, E. K. Fishman, R. H. Hruban, Prevalence of unsuspected pancreatic cysts on MDCT. AJR Am J Roentgenol 191, 802-807 (2008).
2. K. de Jong, C. Y. Nio, J. J. Hermans, M. G. Dijkgraaf, D. J. Gouma, C. H. J. van Eijck, E. van Heel, G. Klass, P. Fockens, M. J. Bruno, High Prevalence of Pancreatic Cysts Detected by Screening Magnetic Resonance Imaging Examinations. Clinical Gastroenterology and Hepatology 8, 806-811 (2010).
3. W. Kimura, H. Nagai, A. Kuroda, T. Muto, Y. Esaki, Analysis of small cystic lesions of the pancreas. Int J Pancreatol 18, 197-206 (1995).
4. K. S. Lee, A. Sekhar, N. M. Rofsky, I. Pedrosa, Prevalence of incidental pancreatic cysts in the adult population on MR imaging. Am J Gastroenterol 105, 2079-2084 (2010).
5. H. Matthaei, R. D. Schulick, R. H. Hruban, A. Maitra, Cystic precursors to invasive pancreatic cancer. Nature Reviews Gastroenterology & Hepatology 8, 141-150 (2011).
6. M. Katz, M. Mortenson, H. Wang, R. Hwang, E. Tamm, G. Staerkel, J. Lee, D. Evans, J. Fleming, Diagnosis and Management of Cystic Neoplasms of the Pancreas: An Evidence-Based Approach. Journal of the American College of Surgeons 207, 106-120 (2008).
7. M. Tanaka, Controversies in the management of pancreatic IPMN. Nature Reviews Gastroenterology & Hepatology 8, 56-60 (2011).
8. R. H. Hruban, M. B. Pitman, D. S. Klimstra, Tumors of the pancreas. Atlas of tumor pathology (American Registry of Pathology and Armed Forces Institute of Pathology, Washington, D.C., ed. Fourth Series, Fascicle 6, (2007).
9. G. Klöppel, M. Kosmahl, Cystic Lesions and Neoplasms of the Pancreas. Pancreatology 1, 8 (2001).
10. M. Tanaka, S. Chari, V. Adsay, C. Fernandez-del Castillo, M. Falconi, M. Shimizu, K. Yamaguchi, K. Yamao, S. Matsuno, International consensus guidelines for management of intraductal papillary mucinous neoplasms and mucinous cystic neoplasms of the pancreas. Pancreatology 6, 17-32 (2006).
11. T. A. Sohn, C. J. Yeo, J. L. Cameron, R. H. Hruban, N. Fukushima, K. A. Campbell, K. D. Lillemoe, Intraductal papillary mucinous neoplasms of the pancreas: an updated experience. Ann Surg 239, 788-797; discussion 797-789 (2004).
12. S. Crippa, C. Fernández-del Castillo, R. Salvia, D. Finkelstein, C. Bassi, I. Domínguez, A. Muzikansky, S. P. Thayer, M. Falconi, M. Mino-Kenudson, Mucin-Producing Neoplasms of the Pancreas: An Analysis of Distinguishing Clinical and Epidemiologic Characteristics. Clinical Gastroenterology and Hepatology 8, 213-219.e214 (2010).
13. G. A. Poultsides, S. Reddy, J. L. Cameron, R. H. Hruban, T. M. Pawlik, N. Ahuja, A. Jain, B. H. Edil, C. A. Iacobuzio-Donahue, R. D. Schulick, C. L. Wolfgang, Histopathologic basis for the favorable survival after resection of intraductal papillary mucinous neoplasm-associated invasive adenocarcinoma of the pancreas. Ann Surg 251, 470-476 (2010).
14. T. A. Sohn, C. J. Yeo, J. L. Cameron, L. Koniaris, S. Kaushal, R. A. Abrams, P. I. Sauter, J. Coleman, R. H. Hruban, K. D. Lillemoe, Resected adenocarcinoma of the pancreas 616 patients results, outcomes, and prognostic indicators. Journal of Gastrointestinal Surgery 4, 13 (2000).
15. R. Salvia, C. Fernandez-del Castillo, C. Bassi, S. P. Thayer, M. Falconi, W. Mantovani, P. Pederzoli, A. L. Warshaw, Main-duct intraductal papillary mucinous neoplasms of the pancreas: clinical predictors of malignancy and long-term survival following resection. Ann Surg 239, 678-685; discussion 685-677 (2004).
16. P. U. Freda, W. K. Chung, N. Matsuoka, J. E. Walsh, M. N. Kanibir, G. Kleinman, Y. Wang, J. N. Bruce, K. D. Post, Analysis of GNAS mutations in 60 growth hormone secreting pituitary tumors: correlation with clinical and pathological characteristics and surgical outcome based on highly sensitive GH and IGF-I criteria for remission. Pituitary 10, 275-282 (2007).
17. N. Kalfa, Activating Mutations of the Stimulatory G Protein in Juvenile Ovarian Granulosa Cell Tumors: A New Prognostic Factor? Journal of Clinical Endocrinology & Metabolism 91, 1842-1847 (2006).
18. M. C. Fragoso, A. C. Latronico, F. M. Carvalho, M. C. Zerbini, J. A. Marcondes, L. M. Araujo, V. S. Lando, E. T. Frazzatto, B. B. Mendonca, S. M. Villares, Activating mutation of the stimulatory G protein (gsp) as a putative cause of ovarian and testicular human stromal Leydig cell tumors. J Clin Endocrinol Metab 83, 2074-2078 (1998).
19. H. Yamasaki, N. Mizusawa, S. Nagahiro, S. Yamada, T. Sano, M. Itakura, K. Yoshimoto, GH-secreting pituitary adenomas infrequently contain inactivating mutations of PRKAR1A and LOH of 17q23-24. Clin Endocrinol (Oxf) 58, 464-470 (2003).
20. L. D. Wood, D. W. Parsons, S. Jones, J. Lin, T. Sjoblom, R. J. Leary, D. Shen, S. M. Boca, T. Barber, J. Ptak, N. Silliman, S. Szabo, Z. Dezso, V. Ustyanksky, T. Nikolskaya, Y. Nikolsky, R. Karchin, P. A. Wilson, J. S. Kaminker, Z. Zhang, R. Croshaw, J. Willis, D. Dawson, M. Shipitsin, J. K. V. Willson, S. Sukumar, K. Polyak, B. H. Park, C. L. Pethiyagoda, P. V. K. Pant, D. G. Ballinger, A. B. Sparks, J. Hartigan, D. R. Smith, E. Suh, N. Papadopoulos, P. Buckhaults, S. D. Markowitz, G. Parmigiani, K. W. Kinzler, V. E. Velculescu, B. Vogelstein, The Genomic Landscapes of Human Breast and Colorectal Cancers. Science 318, 1108-1113 (2007).
21. S. Idziaszczyk, C. H. Wilson, C. G. Smith, D. J. Adams, J. P. Cheadle, Analysis of the frequency of GNAS codon 201 mutations in advanced colorectal cancer. Cancer Genetics and Cytogenetics 202, 67-69 (2010).
22. J.-S. Shin, A. Spillane, E. Wills, W. A. Cooper, PEComa of the retroperitoneum. Pathology 40, 93-95 (2008).
23. I. J. Dahabreh, T. Terasawa, P. J. Castaldi, T. A. Trikalinos, Systematic review: Anti-epidermal growth factor receptor treatment effect modification by KRAS mutations in advanced colorectal cancer. Ann Intern Med 154, 37-49 (2011).

24. C. Almoguera, D. Shibata, K. Forrester, J. Martin, N. Arnheim, M. Perucho, Most human carcinomas of the exocrine pancreas contain mutant c-K-ras genes. Cell 53, 549-554 (1988).

25. S. Fritz, C. Fernandez-del Castillo, M. Mino-Kenudson, S. Crippa, V. Deshpande, G. Y. Lauwers, A. L. Warshaw, S. P. Thayer, A. J. Iafrate, Global Genomic Analysis of Intraductal Papillary Mucinous Neoplasms of the Pancreas Reveals Significant Molecular Differences Compared to Ductal Adenocarcinoma. Annals of Surgery 249, 440-447 (2009).

26. D. Soldini, M. Gugger, E. Burckhardt, A. Kappeler, J. A. Laissue, L. Mazzucchelli, Progressive genomic alterations in intraductal papillary mucinous tumours of the pancreas and morphologically similar lesions of the pancreatic ducts. The Journal of Pathology 199, 453-461 (2003).

27. F. Schönleben, W. Qiu, K. C. Bruckman, N. T. Ciau, X. Li, M. H. Lauerman, H. Frucht, J. A. Chabot, J. D. Allendorf, H. E. Remotti, BRAF and KRAS gene mutations in intraductal papillary mucinous neoplasm/carcinoma (IPMN/IPMC) of the pancreas. Cancer Letters 249, 242-248 (2007).

28. K. Wada, Does "clonal progression" relate to the development of intraductal papillary mucinous tumors of the pancreas? Journal of Gastrointestinal Surgery 8, 289-296 (2004).

29. S. Jones, X. Zhang, D. W. Parsons, J. C. H. Lin, R. J. Leary, P. Angenendt, P. Mankoo, H. Carter, H. Kamiyama, A. Jimeno, S. M. Hong, B. Fu, M. T. Lin, E. S. Calhoun, M. Kamiyama, K. Walter, T. Nikolskaya, Y. Nikolsky, J. Hartigan, D. R. Smith, M. Hidalgo, S. D. Leach, A. P. Klein, E. M. Jaffee, M. Goggins, A. Maitra, C. Iacobuzio-Donahue, J. R. Eshleman, S. E. Kern, R. H. Hruban, R. Karchin, N. Papadopoulos, G. Parmigiani, B. Vogelstein, V. E. Velculescu, K. W. Kinzler, Core Signaling Pathways in Human Pancreatic Cancers Revealed by Global Genomic Analyses. Science 321, 1801-1806 (2008).

30. G. Parmigiani, S. Boca, J. Lin, K. W. Kinzler, V. Velculescu, B. Vogelstein, Design and analysis issues in genome-wide somatic mutation studies of cancer. Genomics 93, 17-21 (2009).

31. F. Schonleben, J. D. Allendorf, W. Qiu, X. Li, D. J. Ho, N. T. Ciau, R. L. Fine, J. A. Chabot, H. E. Remotti, G. H. Su, Mutational analyses of multiple oncogenic pathways in intraductal papillary mucinous neoplasms of the pancreas. Pancreas 36, 168-172 (2008).

32. M. Kitago, M. Ueda, K. Aiura, K. Suzuki, S. Hoshimoto, S. Takahashi, M. Mukai, M. Kitajima, Comparison of K-ras point mutation distributions in intraductal papillary-mucinous tumors and ductal adenocarcinoma of the pancreas. International Journal of Cancer 110, 177-182 (2004).

33. T. Izawa, T. Obara, S. Tanno, Y. Mizukami, N. Yanagawa, Y. Kohgo, Clonality and Field Cancerization in Intraductal Papillary-Mucinous Tumors of the Pancreas. Cancer 92, 11 (2001).

34. F. Diehl, M. Li, Y. He, K. W. Kinzler, B. Vogelstein, D. Dressman, BEAMing: single-molecule PCR on microparticles in water-in-oil emulsions. Nature Methods 3, 551-559 (2006).

35. H. Fujii, M. Inagaki, S. Kasai, N. Miyokawa, Y. Tokusashi, E. Gabrielson, R. H. Hruban, Genetic progression and heterogeneity in intraductal papillary-mucinous neoplasms of the pancreas. American Journal of Pathology 151, 8 (1997).

36. B. Taouli, V. r. Vilgrain, M.-P. Vullierme, B. t. Terris, A. Denys, A. Sauvanet, P. Hammel, Y. Menu, Intraductal Papillary Mucinous Tumors of the Pancreas: Helical CT with Histopathologic Correlation. Radiology 217, 8 (2000).

37. A. Diaz, M. Danon, J. Crawford, McCune-Albright syndrome and disorders due to activating mutations of GNAS1. J Pediatr Endocrinol Metab 20, 853-880 (2007).

38. A. Lania, A. Spada, G-protein and signalling in pituitary tumours. Horm Res 71 Suppl 2, 95-100 (2009).

39. A. G. Lania, G. Mantovani, A. Spada, Mechanisms of disease: Mutations of G proteins and G-protein-coupled receptors in endocrine diseases. Nat Clin Pract Endocrinol Metab 2, 681-693 (2006).

40. D. Shibata, J. Schaeffer, Z. H. Li, G. Capella, M. Perucho, Genetic heterogeneity of the c-K-ras locus in colorectal adenomas but not in adenocarcinomas. J Natl Cancer Inst 85, 1058-1063 (1993).

41. S. Jones, W. D. Chen, G. Parmigiani, F. Diehl, N. Beerenwinkel, T. Antal, A. Traulsen, M. A. Nowak, C. Siegel, V. E. Velculescu, K. W. Kinzler, B. Vogelstein, J. Willis, S. D. Markowitz, Comparative lesion sequencing provides insights into tumor evolution. Proc Natl Acad Sci USA 105, 4283-4288 (2008).

42. C. Correa-Gallego, C. R. Ferrone, S. P. Thayer, J. A. Wargo, A. L. Warshaw, C. Fernández-del Castillo, Incidental Pancreatic Cysts: Do We Really Know What We Are Watching? Pancreatology 10, 144-150 (2010).

43. J. F. Tseng, A. L. Warshaw, D. V. Sahani, G. Y. Lauwers, D. W. Rattner, C. F.-d. Castillo, Serous Cystadenoma of the Pancreas. Transactions of the . . . Meeting of the American Surgical Association 123, 111-118 (2005).

44. S.-M. Hong, D. Kelly, M. Griffith, N. Omura, A. Li, C.-P. Li, R. H. Hruban, M. Goggins, Multiple genes are hypermethylated in intraductal papillary mucinous neoplasms of the pancreas. Mod Pathol 21, 9 (2008).

45. P. J. Allen, L.-X. Qin, L. Tang, D. Klimstra, M. F. Brennan, A. Lokshin, Pancreatic Cyst Fluid Protein Expression Profiling for Discriminating Between Serous Cystadenoma and Intraductal Papillary Mucinous Neoplasm. Annals of Surgery 250, 754-760 (2009).

46. E. Ke, B. B. Patel, T. Liu, X.-M. Li, O. Haluszka, J. P. Hoffman, H. Ehya, N. A. Young, J. C. Watson, D. S. Weinberg, M. T. Nguyen, S. J. Cohen, N. J. Meropol, S. Litwin, J. L. Tokar, A. T. Yeung, Proteomic Analyses of Pancreatic Cyst Fluids. Pancreas 38, 10 (2009).

47. A. Khalid, M. Zahid, S. D. Finkelstein, J. K. LeBlanc, N. Kaushik, N. Ahmad, W. R. Brugge, S. A. Edmundowicz, R. H. Hawes, K. M. McGrath, Pancreatic cyst fluid DNA analysis in evaluating pancreatic cysts: a report of the PANDA study. Gastrointest Endosc 69, 1095-1102 (2009).

48. M. S. Sawhney, S. Devarajan, P. O'Farrel, M. S. Cury, R. Kundu, C. M. Vollmer, A. Brown, R. Chuttani, D. K. Pleskow, Comparison of carcinoembryonic antigen and molecular analysis in pancreatic cyst fluid. Gastrointestinal Endoscopy 69, 1106-1110 (2009).

49. K. E. Schoedel, S. D. Finkelstein, N. P. Ohori, K-Ras and microsatellite marker analysis of fine-needle aspirates from intraductal papillary mucinous neoplasms of the pancreas. Diagnostic Cytopathology 34, 605-608 (2006).

50. D. Bartsch, D. Bastian, P. Barth, A. Schudy, C. Nies, O. Kisker, H. J. Wagner, M. Rothmund, K-ras oncogene mutations indicate malignancy in cystic tumors of the pancreas. Ann Surg 228, 79-86 (1998).

51. M. Al-Haddad, M. B. Wallace, T. A. Woodward, S. A. Gross, C. M. Hodgens, R. D. Toton, M. Raimondo, The safety of fine-needle aspiration guided by endoscopic ultrasound: a prospective study. Endoscopy 40, 204-208 (2008).
52. D. V. Sahani, R. Kadavigere, A. Saokar, C. Fernandez-del Castillo, W. R. Brugge, P. F. Hahn, Cystic pancreatic lesions: a simple imaging-based classification system for guiding management. Radiographics 25, 1471-1484 (2005).
53. F. T. Bosman, F. Carneiro, R. H. Hruban, N. D. Thiese, WHO Classification of Tumours of the Digestive system. (IARC Press, Lyon, ed. 4, 2010), vol. 3.
54. T. Furukawa, G. Kloppel, N. Volkan Adsay, J. Albores-Saavedra, N. Fukushima, A. Horii, R. H. Hruban, Y. Kato, D. S. Klimstra, D. S. Longnecker, J. Luttges, G. J. Offerhaus, M. Shimizu, M. Sunamura, A. Suriawinata, K. Takaori, S. Yonezawa, Classification of types of intraductal papillary-mucinous neoplasm of the pancreas: a consensus study. Virchows Arch 447, 794-799 (2005).
55. C. Rago, D. L. Huso, F. Diehl, B. Karim, G. Liu, N. Papadopoulos, Y. Samuels, V. E. Velculescu, B. Vogelstein, K. W. Kinzler, L. A. Diaz, Jr., Serial Assessment of Human Tumor Burdens in Mice by the Analysis of Circulating DNA. Cancer Res 67, 9364-9370 (2007).
56. F. Diehl, K. Schmidt, M. A. Choti, K. Romans, S. Goodman, M. Li, K. Thornton, N. Agrawal, L. Sokoll, S. A. Szabo, K. W. Kinzler, B. Vogelstein, L. A. Diaz Jr, Circulating mutant DNA to assess tumor dynamics. Nature Medicine 14, 985-990 (2007).
57. D. S. Herman, G. K. Hovingh, O. Iartchouk, H. L. Rehm, R. Kucherlapati, J. G. Seidman, C. E. Seidman, Filter-based hybridization capture of subgenomes enables resequencing and copy-number detection. Nature Methods 6, 507-510 (2009).
58. C. Fouquet, M. Antoine, P. Tisserand, R. Favis, M. Wislez, F. Commo, N. Rabbe, M. F. Carette, B. Milleron, F. Barany, J. Cadranel, G. Zalcman, T. Soussi, Rapid and sensitive p53 alteration analysis in biopsies from lung cancer patients using a functional assay and a universal oligonucleotide array: a prospective study. Clin Cancer Res 10, 3479-3489 (2004).
59. S. M. Dong, G. Traverso, C. Johnson, L. Geng, R. Favis, K. Boynton, K. Hibi, S. N. Goodman, M. D'Allessio, P. Paty, S. R. Hamilton, D. Sidransky, F. Barany, B. Levin, A. Shuber, K. W. Kinzler, B. Vogelstein, J. Jen, Detecting Colorectal Cancer in Stool With the Use of Multiple Genetic Targets. J Natl Cancer Inst 93, 858-865. (2001).
60. J. Luo, D. E. Bergstrom, F. Barany, Improving the fidelity of *Thermus thermophilus* DNA ligase. Nucleic Acids Res 24, 3071-3078 (1996).
61. C. Shi, S. H. Eshleman, D. Jones, N. Fukushima, L. Hua, A. R. Parker, C. J. Yeo, R. H. Hruban, M. G. Goggins, J. R. Eshleman, LigAmp for sensitive detection of single-nucleotide differences. Nat Methods 1, 141-147 (2004).
62. F. Diehl, K. Schmidt, M. A. Choti, K. Romans, S. Goodman, M. Li, K. Thornton, N. Agrawal, L. Sokoll, S. A. Szabo, K. W. Kinzler, B. Vogelstein, L. A. Diaz, Jr., Circulating mutant DNA to assess tumor dynamics. Nat Med 14, 985-990 (2008).
63. T. S. L. StataCorp. 2009. Stata Statistical Software: Release 11. College Station.

The invention claimed is:

1. A method for enriching a sample comprising nucleic acids for target nucleic acid analytes, comprising the steps of:
synthesizing a set of probes for one or more analytes of interest, wherein the probes are complementary to plus or minus strands of a target nucleic acid analyte, wherein each probe has a 5' universal priming site and a 3' universal priming site;
amplifying the set of probes using primers complementary to the 5' universal priming site and primers complementary to the 3' universal priming site;
ligating the amplified probes to form double-stranded concatamers;
isothermally amplifying the double-stranded concatamers to form single-stranded amplified concatamers;
binding the single-stranded amplified concatamers to a solid support;
contacting the solid support with the sample comprising nucleic acids under hybridization conditions so that complementary nucleic acids in the sample are captured on the solid support and non-complementary nucleic acids are removed;
eluting captured nucleic acids from the solid support.

2. A method for enriching a sample for target nucleic acid analytes, comprising the steps of:
synthesizing a set of probes for one or more analytes of interest, wherein the probes are complementary to plus or minus strands of a target nucleic acid analyte, wherein each probe has a 5' universal priming site and a 3' universal priming site;
amplifying the set of probes using primers complementary to the 5' universal priming site and primers complementary to the 3' universal priming site;
ligating the amplified probes to form double-stranded concatamers;
isothermally amplifying the double-stranded concatamers in the presence of biotinylated nucleotides, such that biotinylated nucleotides are incorporated into amplified, single-stranded concatamers;
contacting the amplified, single-stranded concatamers with the sample nucleic acids to form a mixture, and subjecting the mixture to hybridization conditions so that complementary nucleic acids in the mixture hybridize to the amplified, single-stranded concatamers;
contacting the mixture with a solid support so that hybridized nucleic acids are captured on the solid support, wherein the solid support comprises avidin or streptavidin;
washing the solid support to remove nucleic acids which do not comprise biotin;
eluting captured nucleic acids from the solid support.

3. The method of claim 1 further comprising the step of: analyzing nucleotide sequence of the eluted, captured nucleic acids.

4. The method of claim 3 wherein the analyzing is massively parallel.

5. The method of claim 2 further comprising: analyzing nucleotide sequence of the eluted, captured nucleic acids.

6. The method of claim 5 wherein the analyzing is massively parallel.

7. The method of claim 1 further comprising the step of: amplifying the eluted, captured nucleic acids.

8. The method of claim 2 further comprising the step of: amplifying the eluted, captured nucleic acids.

9. The method of claim 1 wherein the set of probes are synthesized on a solid array.

10. The method of claim 9 wherein the set of probes are cleaved from the solid array to form an aqueous solution comprising the set of probes.

11. The method of claim 2 wherein the set of probes are synthesized on a solid array.

12. The method of claim 11 wherein the set of probes are cleaved from the solid array to form an aqueous solution comprising the set of probes.

13. The method of claim 1 wherein the probes are complementary to both plus and minus strands of a target nucleic acid analyte.

14. The method of claim 1 wherein probes for one analyte overlap with a register of three nucleotide displacement.

15. The method of claim 13 wherein probes for one analyte overlap with a register of three nucleotide displacement.

16. The method of claim 1 wherein the solid support is a filter.

17. The method of claim 1 wherein the solid support is a bead.

18. The method of claim 2 wherein the probes are complementary to both plus and minus strands of a target nucleic acid analyte.

19. The method of claim 2 wherein probes for one analyte overlap with a register of three nucleotide displacement.

20. The method of claim 18 wherein probes for one analyte overlap with a register of three nucleotide displacement.

21. The method of claim 2 wherein the solid support is a filter.

22. The method of claim 2 wherein the solid support is a bead.

* * * * *

UNITED STATES PATENT AND TRADEMARK OFFICE
CERTIFICATE OF CORRECTION

PATENT NO. : 9,670,527 B2
APPLICATION NO. : 14/130007
DATED : June 6, 2017
INVENTOR(S) : Bert Vogelstein et al.

Page 1 of 1

It is certified that error appears in the above-identified patent and that said Letters Patent is hereby corrected as shown below:

In the Specification

Column 1 Lines 4-7 (government support statement) please replace with the following:

STATEMENT OF GOVERNMENTAL INTEREST
This invention was made with government support under grant numbers CA043460, CA057345, CA062924, awarded by the National Institutes of Health. The government has certain rights in the invention.

Signed and Sealed this
Sixth Day of February, 2018

Joseph Matal
*Performing the Functions and Duties of the*
*Under Secretary of Commerce for Intellectual Property and*
*Director of the United States Patent and Trademark Office*

SEQUENCE LISTING

```
<160> NUMBER OF SEQ ID NOS: 194

<210> SEQ ID NO 1
<211> LENGTH: 60
<212> TYPE: DNA
<213> ORGANISM: Artificial Sequence
<220> FEATURE:
<223> OTHER INFORMATION: Probe
<221> NAME/KEY: misc_feature
<222> LOCATION: (13)...(48)
<223> OTHER INFORMATION: 36 bases from a genomic region of interest
<221> NAME/KEY: misc_feature
<222> LOCATION: (1)...(60)
<223> OTHER INFORMATION: n = A,T,C or G

<400> SEQUENCE: 1
tcccgcgacg acnnnnnnnn nnnnnnnnnn nnnnnnnnnn nnnnnnnngc tggagtcgcg    60

<210> SEQ ID NO 2
<211> LENGTH: 15
<212> TYPE: DNA
<213> ORGANISM: Artificial Sequence
<220> FEATURE:
<223> OTHER INFORMATION: Probe

<400> SEQUENCE: 2
tgatcccgcg acgac                                                     15

<210> SEQ ID NO 3
<211> LENGTH: 15
<212> TYPE: DNA
<213> ORGANISM: Artificial Sequence
<220> FEATURE:
<223> OTHER INFORMATION: Probe

<400> SEQUENCE: 3
```

```
gaccgcgact ccagc                                                    15

<210> SEQ ID NO 4
<211> LENGTH: 20
<212> TYPE: DNA
<213> ORGANISM: Artificial Sequence
<220> FEATURE:
<223> OTHER INFORMATION: Probe

<400> SEQUENCE: 4
ggctttggtg agatccattg                                               20

<210> SEQ ID NO 5
<211> LENGTH: 20
<212> TYPE: DNA
<213> ORGANISM: Artificial Sequence
<220> FEATURE:
<223> OTHER INFORMATION: Probe

<400> SEQUENCE: 5
tccacctgga acttggtctc                                               20

<210> SEQ ID NO 6
<211> LENGTH: 26
<212> TYPE: DNA
<213> ORGANISM: Artificial Sequence
<220> FEATURE:
<223> OTHER INFORMATION: Probe

<400> SEQUENCE: 6
gatcatattc gtccacaaaa tgattc                                        26

<210> SEQ ID NO 7
<211> LENGTH: 27
<212> TYPE: DNA
<213> ORGANISM: Artificial Sequence
<220> FEATURE:
<223> OTHER INFORMATION: Probe

<400> SEQUENCE: 7
tgactgaata taaacttgtg gtagttg                                       27

<210> SEQ ID NO 8
<211> LENGTH: 30
<212> TYPE: DNA
<213> ORGANISM: Artificial Sequence
<220> FEATURE:
<223> OTHER INFORMATION: Probe

<400> SEQUENCE: 8
atggagaact tgacgtcctg ttcgctgccg                                    30

<210> SEQ ID NO 9
<211> LENGTH: 10
<212> TYPE: DNA
<213> ORGANISM: Artificial Sequence
<220> FEATURE:
<223> OTHER INFORMATION: Probe

<400> SEQUENCE: 9
ttcgctgcca                                                          10

<210> SEQ ID NO 10
<211> LENGTH: 32
<212> TYPE: DNA
```

```
<213> ORGANISM: Artificial Sequence
<220> FEATURE:
<223> OTHER INFORMATION: Probe

<400> SEQUENCE: 10
tgtcctgact tcggtgtcca ctagtcatgc tt                                    32

<210> SEQ ID NO 11
<211> LENGTH: 30
<212> TYPE: DNA
<213> ORGANISM: Artificial Sequence
<220> FEATURE:
<223> OTHER INFORMATION: Probe

<400> SEQUENCE: 11
atggagaact tgacgtccac cttcgctgcc                                       30

<210> SEQ ID NO 12
<211> LENGTH: 10
<212> TYPE: DNA
<213> ORGANISM: Artificial Sequence
<220> FEATURE:
<223> OTHER INFORMATION: Probe

<400> SEQUENCE: 12
cttcgctgct                                                             10

<210> SEQ ID NO 13
<211> LENGTH: 32
<212> TYPE: DNA
<213> ORGANISM: Artificial Sequence
<220> FEATURE:
<223> OTHER INFORMATION: Probe

<400> SEQUENCE: 13
gtgtcctgac ttggtgtcca ctagtcatgc tt                                    32

<210> SEQ ID NO 14
<211> LENGTH: 29
<212> TYPE: DNA
<213> ORGANISM: Artificial Sequence
<220> FEATURE:
<223> OTHER INFORMATION: Probe

<400> SEQUENCE: 14
atggagaact tgacgtcctc ctacgccac                                        29

<210> SEQ ID NO 15
<211> LENGTH: 12
<212> TYPE: DNA
<213> ORGANISM: Artificial Sequence
<220> FEATURE:
<223> OTHER INFORMATION: Probe

<400> SEQUENCE: 15
tgcctacgcc at                                                          12

<210> SEQ ID NO 16
<211> LENGTH: 32
<212> TYPE: DNA
<213> ORGANISM: Artificial Sequence
<220> FEATURE:
<223> OTHER INFORMATION: Probe

<400> SEQUENCE: 16
cagctccaac taggtgtcca ctagtcatgc tt                                    32
```

```
<210> SEQ ID NO 17
<211> LENGTH: 30
<212> TYPE: DNA
<213> ORGANISM: Artificial Sequence
<220> FEATURE:
<223> OTHER INFORMATION: Probe

<400> SEQUENCE: 17
tcccgcgaaa ttaatacgag ctacgccacc                                    30

<210> SEQ ID NO 18
<211> LENGTH: 10
<212> TYPE: DNA
<213> ORGANISM: Artificial Sequence
<220> FEATURE:
<223> OTHER INFORMATION: Probe

<400> SEQUENCE: 18
ctacgccacg                                                          10

<210> SEQ ID NO 19
<211> LENGTH: 35
<212> TYPE: DNA
<213> ORGANISM: Artificial Sequence
<220> FEATURE:
<223> OTHER INFORMATION: Probe

<400> SEQUENCE: 19
agctccaact accacggtgt ccactagtca tgctt                              35

<210> SEQ ID NO 20
<211> LENGTH: 29
<212> TYPE: DNA
<213> ORGANISM: Artificial Sequence
<220> FEATURE:
<223> OTHER INFORMATION: Probe

<400> SEQUENCE: 20
atggagaact tgacgtcctc ctacgccac                                     29

<210> SEQ ID NO 21
<211> LENGTH: 10
<212> TYPE: DNA
<213> ORGANISM: Artificial Sequence
<220> FEATURE:
<223> OTHER INFORMATION: Probe

<400> SEQUENCE: 21
cctacgccaa                                                          10

<210> SEQ ID NO 22
<211> LENGTH: 32
<212> TYPE: DNA
<213> ORGANISM: Artificial Sequence
<220> FEATURE:
<223> OTHER INFORMATION: Probe

<400> SEQUENCE: 22
cagctccaac taggtgtcca ctagtcatgc tt                                 32

<210> SEQ ID NO 23
<211> LENGTH: 18
<212> TYPE: DNA
<213> ORGANISM: Artificial Sequence
<220> FEATURE:
```

```
<223> OTHER INFORMATION: Probe

<400> SEQUENCE: 23
ctgaaacaaa attgaggt                                                 18

<210> SEQ ID NO 24
<211> LENGTH: 15
<212> TYPE: DNA
<213> ORGANISM: Artificial Sequence
<220> FEATURE:
<223> OTHER INFORMATION: Probe

<400> SEQUENCE: 24
aggacacggc agcga                                                    15

<210> SEQ ID NO 25
<211> LENGTH: 15
<212> TYPE: DNA
<213> ORGANISM: Artificial Sequence
<220> FEATURE:
<223> OTHER INFORMATION: Probe

<400> SEQUENCE: 25
aggacacagc agcga                                                    15

<210> SEQ ID NO 26
<211> LENGTH: 18
<212> TYPE: DNA
<213> ORGANISM: Artificial Sequence
<220> FEATURE:
<223> OTHER INFORMATION: Probe

<400> SEQUENCE: 26
ctgaaacaaa attgaggt                                                 18

<210> SEQ ID NO 27
<211> LENGTH: 15
<212> TYPE: DNA
<213> ORGANISM: Artificial Sequence
<220> FEATURE:
<223> OTHER INFORMATION: Probe

<400> SEQUENCE: 27
caggacacgg cagcg                                                    15

<210> SEQ ID NO 28
<211> LENGTH: 15
<212> TYPE: DNA
<213> ORGANISM: Artificial Sequence
<220> FEATURE:
<223> OTHER INFORMATION: Probe

<400> SEQUENCE: 28
caggacatgg cagcg                                                    15

<210> SEQ ID NO 29
<211> LENGTH: 19
<212> TYPE: DNA
<213> ORGANISM: Artificial Sequence
<220> FEATURE:
<223> OTHER INFORMATION: Probe

<400> SEQUENCE: 29
tgacgataca gctaattca                                                19
```

```
<210> SEQ ID NO 30
<211> LENGTH: 15
<212> TYPE: DNA
<213> ORGANISM: Artificial Sequence
<220> FEATURE:
<223> OTHER INFORMATION: Probe

<400> SEQUENCE: 30
ggagctggtg gcgta                                                        15

<210> SEQ ID NO 31
<211> LENGTH: 15
<212> TYPE: DNA
<213> ORGANISM: Artificial Sequence
<220> FEATURE:
<223> OTHER INFORMATION: Probe

<400> SEQUENCE: 31
ggagctgatg gcgta                                                        15

<210> SEQ ID NO 32
<211> LENGTH: 19
<212> TYPE: DNA
<213> ORGANISM: Artificial Sequence
<220> FEATURE:
<223> OTHER INFORMATION: Probe

<400> SEQUENCE: 32
tgacgataca gctaattca                                                    19

<210> SEQ ID NO 33
<211> LENGTH: 15
<212> TYPE: DNA
<213> ORGANISM: Artificial Sequence
<220> FEATURE:
<223> OTHER INFORMATION: Probe

<400> SEQUENCE: 33
ggagctggtg gcgta                                                        15

<210> SEQ ID NO 34
<211> LENGTH: 15
<212> TYPE: DNA
<213> ORGANISM: Artificial Sequence
<220> FEATURE:
<223> OTHER INFORMATION: Probe

<400> SEQUENCE: 34
ggagctgttg gcgta                                                        15

<210> SEQ ID NO 35
<211> LENGTH: 19
<212> TYPE: DNA
<213> ORGANISM: Artificial Sequence
<220> FEATURE:
<223> OTHER INFORMATION: Probe

<400> SEQUENCE: 35
tgacgataca gctaattca                                                    19

<210> SEQ ID NO 36
<211> LENGTH: 15
<212> TYPE: DNA
<213> ORGANISM: Artificial Sequence
<220> FEATURE:
<223> OTHER INFORMATION: Probe
```

```
<400> SEQUENCE: 36
tggagctggt ggcgt                                                    15

<210> SEQ ID NO 37
<211> LENGTH: 15
<212> TYPE: DNA
<213> ORGANISM: Artificial Sequence
<220> FEATURE:
<223> OTHER INFORMATION: Probe

<400> SEQUENCE: 37
tggagctcgt ggcgt                                                    15

<210> SEQ ID NO 38
<211> LENGTH: 60
<212> TYPE: DNA
<213> ORGANISM: Artificial Sequence
<220> FEATURE:
<223> OTHER INFORMATION: probes

<400> SEQUENCE: 38
tcccgcgacg actctcagtg tctgacttcg acaacgccaa gggcctcagc tggagtcgcg   60

<210> SEQ ID NO 39
<211> LENGTH: 60
<212> TYPE: DNA
<213> ORGANISM: Artificial Sequence
<220> FEATURE:
<223> OTHER INFORMATION: probes

<400> SEQUENCE: 39
tcccgcgacg accagtgtct gacttcgaca acgccaaggg cctcaacggc tggagtcgcg   60

<210> SEQ ID NO 40
<211> LENGTH: 60
<212> TYPE: DNA
<213> ORGANISM: Artificial Sequence
<220> FEATURE:
<223> OTHER INFORMATION: probes

<400> SEQUENCE: 40
tcccgcgacg actgtctgac ttcgacaacg ccaagggcct caacgtgagc tggagtcgcg   60

<210> SEQ ID NO 41
<211> LENGTH: 60
<212> TYPE: DNA
<213> ORGANISM: Artificial Sequence
<220> FEATURE:
<223> OTHER INFORMATION: probes

<400> SEQUENCE: 41
tcccgcgacg acctgacttc gacaacgcca agggcctcaa cgtgaagcgc tggagtcgcg   60

<210> SEQ ID NO 42
<211> LENGTH: 60
<212> TYPE: DNA
<213> ORGANISM: Artificial Sequence
<220> FEATURE:
<223> OTHER INFORMATION: probes

<400> SEQUENCE: 42
tcccgcgacg acacttcgac aacgccaagg gcctcaacgt gaagcactgc tggagtcgcg   60

<210> SEQ ID NO 43
<211> LENGTH: 60
```

```
<212> TYPE: DNA
<213> ORGANISM: Artificial Sequence
<220> FEATURE:
<223> OTHER INFORMATION: probes

<400> SEQUENCE: 43
tcccgcgacg actcgacaac gccaagggcc tcaacgtgaa gcactacagc tggagtcgcg    60

<210> SEQ ID NO 44
<211> LENGTH: 60
<212> TYPE: DNA
<213> ORGANISM: Artificial Sequence
<220> FEATURE:
<223> OTHER INFORMATION: probes

<400> SEQUENCE: 44
tcccgcgacg acacaacgcc aagggcctca acgtgaagca ctacaagagc tggagtcgcg    60

<210> SEQ ID NO 45
<211> LENGTH: 60
<212> TYPE: DNA
<213> ORGANISM: Artificial Sequence
<220> FEATURE:
<223> OTHER INFORMATION: probes

<400> SEQUENCE: 45
tcccgcgacg acacgccaag ggcctcaacg tgaagcacta caagatccgc tggagtcgcg    60

<210> SEQ ID NO 46
<211> LENGTH: 60
<212> TYPE: DNA
<213> ORGANISM: Artificial Sequence
<220> FEATURE:
<223> OTHER INFORMATION: probes

<400> SEQUENCE: 46
tcccgcgacg acccaagggc ctcaacgtga agcactacaa gatccgcagc tggagtcgcg    60

<210> SEQ ID NO 47
<211> LENGTH: 60
<212> TYPE: DNA
<213> ORGANISM: Artificial Sequence
<220> FEATURE:
<223> OTHER INFORMATION: probes

<400> SEQUENCE: 47
tcccgcgacg acagggcctc aacgtgaagc actacaagat ccgcaagcgc tggagtcgcg    60

<210> SEQ ID NO 48
<211> LENGTH: 60
<212> TYPE: DNA
<213> ORGANISM: Artificial Sequence
<220> FEATURE:
<223> OTHER INFORMATION: probes

<400> SEQUENCE: 48
tcccgcgacg acgcctcaac gtgaagcact acaagatccg caagctgggc tggagtcgcg    60

<210> SEQ ID NO 49
<211> LENGTH: 60
<212> TYPE: DNA
<213> ORGANISM: Artificial Sequence
<220> FEATURE:
<223> OTHER INFORMATION: probes

<400> SEQUENCE: 49
```
tcccgcgacg actcaacgtg aagcactaca agatccgcaa gctggacagc tggagtcgcg    60

<210> SEQ ID NO 50
<211> LENGTH: 60
<212> TYPE: DNA
<213> ORGANISM: Artificial Sequence
<220> FEATURE:
<223> OTHER INFORMATION: probes

<400> SEQUENCE: 50
tcccgcgacg acacgtgaag cactacaaga tccgcaagct ggacagcggc tggagtcgcg    60

<210> SEQ ID NO 51
<211> LENGTH: 60
<212> TYPE: DNA
<213> ORGANISM: Artificial Sequence
<220> FEATURE:
<223> OTHER INFORMATION: probes

<400> SEQUENCE: 51
tcccgcgacg actgaagcac tacaagatcc gcaagctgga cagcggcggc tggagtcgcg    60

<210> SEQ ID NO 52
<211> LENGTH: 60
<212> TYPE: DNA
<213> ORGANISM: Artificial Sequence
<220> FEATURE:
<223> OTHER INFORMATION: probes

<400> SEQUENCE: 52
tcccgcgacg acagcactac aagatccgca agctggacag cggcggctgc tggagtcgcg    60

<210> SEQ ID NO 53
<211> LENGTH: 60
<212> TYPE: DNA
<213> ORGANISM: Artificial Sequence
<220> FEATURE:
<223> OTHER INFORMATION: probes

<400> SEQUENCE: 53
tcccgcgacg acactacaag atccgcaagc tggacagcgg cggcttctgc tggagtcgcg    60

<210> SEQ ID NO 54
<211> LENGTH: 60
<212> TYPE: DNA
<213> ORGANISM: Artificial Sequence
<220> FEATURE:
<223> OTHER INFORMATION: probes

<400> SEQUENCE: 54
tcccgcgacg acacaagatc cgcaagctgg acagcggcgg cttctacagc tggagtcgcg    60

<210> SEQ ID NO 55
<211> LENGTH: 60
<212> TYPE: DNA
<213> ORGANISM: Artificial Sequence
<220> FEATURE:
<223> OTHER INFORMATION: probes

<400> SEQUENCE: 55
tcccgcgacg acagatccgc aagctggaca gcggcggctt ctacatcagc tggagtcgcg    60

<210> SEQ ID NO 56
<211> LENGTH: 60
<212> TYPE: DNA
<213> ORGANISM: Artificial Sequence

```
<220> FEATURE:
<223> OTHER INFORMATION: probes

<400> SEQUENCE: 56
tcccgcgacg actccgcaag ctggacagcg gcggcttcta catcacctgc tggagtcgcg      60

<210> SEQ ID NO 57
<211> LENGTH: 60
<212> TYPE: DNA
<213> ORGANISM: Artificial Sequence
<220> FEATURE:
<223> OTHER INFORMATION: probes

<400> SEQUENCE: 57
tcccgcgacg acgcaagctg acagcggcg gcttctacat cacctcccgc tggagtcgcg       60

<210> SEQ ID NO 58
<211> LENGTH: 60
<212> TYPE: DNA
<213> ORGANISM: Artificial Sequence
<220> FEATURE:
<223> OTHER INFORMATION: probes

<400> SEQUENCE: 58
tcccgcgacg acagctggac agcggcggct tctacatcac ctcccgcagc tggagtcgcg      60

<210> SEQ ID NO 59
<211> LENGTH: 60
<212> TYPE: DNA
<213> ORGANISM: Artificial Sequence
<220> FEATURE:
<223> OTHER INFORMATION: probes

<400> SEQUENCE: 59
tcccgcgacg actggacagc ggcggcttct acatcacctc ccgcacccgc tggagtcgcg      60

<210> SEQ ID NO 60
<211> LENGTH: 60
<212> TYPE: DNA
<213> ORGANISM: Artificial Sequence
<220> FEATURE:
<223> OTHER INFORMATION: probes

<400> SEQUENCE: 60
tcccgcgacg acacagcggc ggcttctaca tcacctcccg cacccagtgc tggagtcgcg      60

<210> SEQ ID NO 61
<211> LENGTH: 60
<212> TYPE: DNA
<213> ORGANISM: Artificial Sequence
<220> FEATURE:
<223> OTHER INFORMATION: probes

<400> SEQUENCE: 61
tcccgcgacg acgcggcggc ttctacatca cctcccgcac ccagttcagc tggagtcgcg      60

<210> SEQ ID NO 62
<211> LENGTH: 60
<212> TYPE: DNA
<213> ORGANISM: Artificial Sequence
<220> FEATURE:
<223> OTHER INFORMATION: probes

<400> SEQUENCE: 62
tcccgcgacg acgcggcttc tacatcacct cccgcaccca gttcaacagc tggagtcgcg      60
```

<210> SEQ ID NO 63
<211> LENGTH: 60
<212> TYPE: DNA
<213> ORGANISM: Artificial Sequence
<220> FEATURE:
<223> OTHER INFORMATION: probes

<400> SEQUENCE: 63
tcccgcgacg acgcttctac atcacctccc gcacccagtt caacagccgc tggagtcgcg    60

<210> SEQ ID NO 64
<211> LENGTH: 60
<212> TYPE: DNA
<213> ORGANISM: Artificial Sequence
<220> FEATURE:
<223> OTHER INFORMATION: probes

<400> SEQUENCE: 64
tcccgcgacg actctacatc acctcccgca cccagttcaa cagcctgcgc tggagtcgcg    60

<210> SEQ ID NO 65
<211> LENGTH: 60
<212> TYPE: DNA
<213> ORGANISM: Artificial Sequence
<220> FEATURE:
<223> OTHER INFORMATION: probes

<400> SEQUENCE: 65
tcccgcgacg acacatcacc tcccgcaccc agttcaacag cctgcagcgc tggagtcgcg    60

<210> SEQ ID NO 66
<211> LENGTH: 60
<212> TYPE: DNA
<213> ORGANISM: Artificial Sequence
<220> FEATURE:
<223> OTHER INFORMATION: probes

<400> SEQUENCE: 66
tcccgcgacg actcacctcc cgcacccagt tcaacagcct gcagcagcgc tggagtcgcg    60

<210> SEQ ID NO 67
<211> LENGTH: 60
<212> TYPE: DNA
<213> ORGANISM: Artificial Sequence
<220> FEATURE:
<223> OTHER INFORMATION: probes

<400> SEQUENCE: 67
tcccgcgacg accctcccgc acccagttca acagcctgca gcagctgggc tggagtcgcg    60

<210> SEQ ID NO 68
<211> LENGTH: 60
<212> TYPE: DNA
<213> ORGANISM: Artificial Sequence
<220> FEATURE:
<223> OTHER INFORMATION: probes

<400> SEQUENCE: 68
tcccgcgacg accccgcacc cagttcaaca gcctgcagca gctggtgggc tggagtcgcg    60

<210> SEQ ID NO 69
<211> LENGTH: 60
<212> TYPE: DNA
<213> ORGANISM: Artificial Sequence
<220> FEATURE:
<223> OTHER INFORMATION: probes

<400> SEQUENCE: 69
tcccgcgacg actgccgtgt cctgacttct ggaatctttg agaccaaggc tggagtcgcg    60

<210> SEQ ID NO 70
<211> LENGTH: 60
<212> TYPE: DNA
<213> ORGANISM: Artificial Sequence
<220> FEATURE:
<223> OTHER INFORMATION: probes

<400> SEQUENCE: 70
tcccgcgacg accgtgtcct gacttctgga atctttgaga ccaagttcgc tggagtcgcg    60

<210> SEQ ID NO 71
<211> LENGTH: 60
<212> TYPE: DNA
<213> ORGANISM: Artificial Sequence
<220> FEATURE:
<223> OTHER INFORMATION: probes

<400> SEQUENCE: 71
tcccgcgacg acgtcctgac ttctggaatc tttgagacca gttccaggc tggagtcgcg    60

<210> SEQ ID NO 72
<211> LENGTH: 60
<212> TYPE: DNA
<213> ORGANISM: Artificial Sequence
<220> FEATURE:
<223> OTHER INFORMATION: probes

<400> SEQUENCE: 72
tcccgcgacg acctgacttc tggaatcttt gagaccaagt tccaggtggc tggagtcgcg    60

<210> SEQ ID NO 73
<211> LENGTH: 60
<212> TYPE: DNA
<213> ORGANISM: Artificial Sequence
<220> FEATURE:
<223> OTHER INFORMATION: probes

<400> SEQUENCE: 73
tcccgcgacg acacttctgg aatctttgag accaagttcc aggtggacgc tggagtcgcg    60

<210> SEQ ID NO 74
<211> LENGTH: 60
<212> TYPE: DNA
<213> ORGANISM: Artificial Sequence
<220> FEATURE:
<223> OTHER INFORMATION: probes

<400> SEQUENCE: 74
tcccgcgacg acggcctgtt gcgtctcagc agcagtgcac taaataacgc tggagtcgcg    60

<210> SEQ ID NO 75
<211> LENGTH: 60
<212> TYPE: DNA
<213> ORGANISM: Artificial Sequence
<220> FEATURE:
<223> OTHER INFORMATION: probes

<400> SEQUENCE: 75
tcccgcgacg acctgttgcg tctcagcagc agtgcactaa ataacgaggc tggagtcgcg    60

<210> SEQ ID NO 76

```
<211> LENGTH: 60
<212> TYPE: DNA
<213> ORGANISM: Artificial Sequence
<220> FEATURE:
<223> OTHER INFORMATION: probes

<400> SEQUENCE: 76
tcccgcgacg acttgcgtct cagcagcagt gcactaaata acgagtttgc tggagtcgcg        60

<210> SEQ ID NO 77
<211> LENGTH: 60
<212> TYPE: DNA
<213> ORGANISM: Artificial Sequence
<220> FEATURE:
<223> OTHER INFORMATION: probes

<400> SEQUENCE: 77
tcccgcgacg accgtctcag cagcagtgca ctaaataacg agttttttgc tggagtcgcg        60

<210> SEQ ID NO 78
<211> LENGTH: 60
<212> TYPE: DNA
<213> ORGANISM: Artificial Sequence
<220> FEATURE:
<223> OTHER INFORMATION: probes

<400> SEQUENCE: 78
tcccgcgacg acctcagcag cagtgcacta ataacgagt tttttaccgc tggagtcgcg        60

<210> SEQ ID NO 79
<211> LENGTH: 60
<212> TYPE: DNA
<213> ORGANISM: Artificial Sequence
<220> FEATURE:
<223> OTHER INFORMATION: probes

<400> SEQUENCE: 79
tcccgcgacg acagcagcag tgcactaaat aacgagtttt ttacccatgc tggagtcgcg        60

<210> SEQ ID NO 80
<211> LENGTH: 60
<212> TYPE: DNA
<213> ORGANISM: Artificial Sequence
<220> FEATURE:
<223> OTHER INFORMATION: probes

<400> SEQUENCE: 80
tcccgcgacg acagcagtgc actaaataac gagtttttta cccatgcggc tggagtcgcg        60

<210> SEQ ID NO 81
<211> LENGTH: 60
<212> TYPE: DNA
<213> ORGANISM: Artificial Sequence
<220> FEATURE:
<223> OTHER INFORMATION: probes

<400> SEQUENCE: 81
tcccgcgacg acagtgcact aaataacgag ttttttaccc atgcggctgc tggagtcgcg        60

<210> SEQ ID NO 82
<211> LENGTH: 60
<212> TYPE: DNA
<213> ORGANISM: Artificial Sequence
<220> FEATURE:
<223> OTHER INFORMATION: probes

<400> SEQUENCE: 82
```

-continued tcccgcgacg acgcactaaa taacgagttt tttacccatg cggctcaggc tggagtcgcg    60

<210> SEQ ID NO 83
<211> LENGTH: 60
<212> TYPE: DNA
<213> ORGANISM: Artificial Sequence
<220> FEATURE:
<223> OTHER INFORMATION: probes

<400> SEQUENCE: 83
tcccgcgacg acctaaataa cgagtttttt acccatgcgg ctcagagcgc tggagtcgcg    60

<210> SEQ ID NO 84
<211> LENGTH: 60
<212> TYPE: DNA
<213> ORGANISM: Artificial Sequence
<220> FEATURE:
<223> OTHER INFORMATION: probes

<400> SEQUENCE: 84
tcccgcgacg acaataacga gttttttacc catgcggctc agagctgggc tggagtcgcg    60

<210> SEQ ID NO 85
<211> LENGTH: 60
<212> TYPE: DNA
<213> ORGANISM: Artificial Sequence
<220> FEATURE:
<223> OTHER INFORMATION: probes

<400> SEQUENCE: 85
tcccgcgacg acaacgagtt ttttacccat gcggctcaga gctggcgggc tggagtcgcg    60

<210> SEQ ID NO 86
<211> LENGTH: 60
<212> TYPE: DNA
<213> ORGANISM: Artificial Sequence
<220> FEATURE:
<223> OTHER INFORMATION: probes

<400> SEQUENCE: 86
tcccgcgacg acgagttttt tacccatgcg gctcagagct ggcgggaggc tggagtcgcg    60

<210> SEQ ID NO 87
<211> LENGTH: 60
<212> TYPE: DNA
<213> ORGANISM: Artificial Sequence
<220> FEATURE:
<223> OTHER INFORMATION: probes

<400> SEQUENCE: 87
tcccgcgacg acgtaccacc agggtggcca tcaaaaccct gaagcctggc tggagtcgcg    60

<210> SEQ ID NO 88
<211> LENGTH: 60
<212> TYPE: DNA
<213> ORGANISM: Artificial Sequence
<220> FEATURE:
<223> OTHER INFORMATION: probes

<400> SEQUENCE: 88
tcccgcgacg acccaccagg gtggccatca aaaccctgaa gcctggcagc tggagtcgcg    60

<210> SEQ ID NO 89
<211> LENGTH: 60
<212> TYPE: DNA

```
<213> ORGANISM: Artificial Sequence
<220> FEATURE:
<223> OTHER INFORMATION: probes

<400> SEQUENCE: 89
tcccgcgacg acccagggtg gccatcaaaa ccctgaagcc tggcacgagc tggagtcgcg    60

<210> SEQ ID NO 90
<211> LENGTH: 96
<212> TYPE: DNA
<213> ORGANISM: Artificial Sequence
<220> FEATURE:
<223> OTHER INFORMATION: probes

<400> SEQUENCE: 90
tcccgcgacg acgggtggcc atcaaaaccc tgaagcctgg cacgatgtgc tggagtcgcg    60
tctcagtgtc tgacttcgac aacgccaagg gcctca                              96

<210> SEQ ID NO 91
<211> LENGTH: 36
<212> TYPE: DNA
<213> ORGANISM: Artificial Sequence
<220> FEATURE:
<223> OTHER INFORMATION: probes

<400> SEQUENCE: 91
cagtgtctga cttcgacaac gccaagggcc tcaacg                              36

<210> SEQ ID NO 92
<211> LENGTH: 36
<212> TYPE: DNA
<213> ORGANISM: Artificial Sequence
<220> FEATURE:
<223> OTHER INFORMATION: probes

<400> SEQUENCE: 92
tgtctgactt cgacaacgcc aagggcctca acgtga                              36

<210> SEQ ID NO 93
<211> LENGTH: 36
<212> TYPE: DNA
<213> ORGANISM: Artificial Sequence
<220> FEATURE:
<223> OTHER INFORMATION: probes

<400> SEQUENCE: 93
ctgacttcga caacgccaag ggcctcaacg tgaagc                              36

<210> SEQ ID NO 94
<211> LENGTH: 36
<212> TYPE: DNA
<213> ORGANISM: Artificial Sequence
<220> FEATURE:
<223> OTHER INFORMATION: probes

<400> SEQUENCE: 94
acttcgacaa cgccaagggc ctcaacgtga agcact                              36

<210> SEQ ID NO 95
<211> LENGTH: 36
<212> TYPE: DNA
<213> ORGANISM: Artificial Sequence
<220> FEATURE:
<223> OTHER INFORMATION: probes

<400> SEQUENCE: 95
```

```
tcgacaacgc aagggcctc aacgtgaagc actaca                                36
```

<210> SEQ ID NO 96
<211> LENGTH: 36
<212> TYPE: DNA
<213> ORGANISM: Artificial Sequence
<220> FEATURE:
<223> OTHER INFORMATION: probes

<400> SEQUENCE: 96

```
acaacgccaa gggcctcaac gtgaagcact acaaga                                36
```

<210> SEQ ID NO 97
<211> LENGTH: 36
<212> TYPE: DNA
<213> ORGANISM: Artificial Sequence
<220> FEATURE:
<223> OTHER INFORMATION: probes

<400> SEQUENCE: 97

```
acgccaaggg cctcaacgtg aagcactaca agatcc                                36
```

<210> SEQ ID NO 98
<211> LENGTH: 36
<212> TYPE: DNA
<213> ORGANISM: Artificial Sequence
<220> FEATURE:
<223> OTHER INFORMATION: probes

<400> SEQUENCE: 98

```
ccaagggcct caacgtgaag cactacaaga tccgca                                36
```

<210> SEQ ID NO 99
<211> LENGTH: 36
<212> TYPE: DNA
<213> ORGANISM: Artificial Sequence
<220> FEATURE:
<223> OTHER INFORMATION: probes

<400> SEQUENCE: 99

```
agggcctcaa cgtgaagcac tacaagatcc gcaagc                                36
```

<210> SEQ ID NO 100
<211> LENGTH: 36
<212> TYPE: DNA
<213> ORGANISM: Artificial Sequence
<220> FEATURE:
<223> OTHER INFORMATION: probes

<400> SEQUENCE: 100

```
gcctcaacgt gaagcactac aagatccgca agctgg                                36
```

<210> SEQ ID NO 101
<211> LENGTH: 36
<212> TYPE: DNA
<213> ORGANISM: Artificial Sequence
<220> FEATURE:
<223> OTHER INFORMATION: probes

<400> SEQUENCE: 101

```
tcaacgtgaa gcactacaag atccgcaagc tggaca                                36
```

<210> SEQ ID NO 102
<211> LENGTH: 36
<212> TYPE: DNA

<213> ORGANISM: Artificial Sequence
<220> FEATURE:
<223> OTHER INFORMATION: probes

<400> SEQUENCE: 102
acgtgaagca ctacaagatc cgcaagctgg acagcg                                    36

<210> SEQ ID NO 103
<211> LENGTH: 36
<212> TYPE: DNA
<213> ORGANISM: Artificial Sequence
<220> FEATURE:
<223> OTHER INFORMATION: probes

<400> SEQUENCE: 103
tgaagcacta caagatccgc aagctggaca gcggcg                                    36

<210> SEQ ID NO 104
<211> LENGTH: 36
<212> TYPE: DNA
<213> ORGANISM: Artificial Sequence
<220> FEATURE:
<223> OTHER INFORMATION: probes

<400> SEQUENCE: 104
agcactacaa gatccgcaag ctggacagcg gcggct                                    36

<210> SEQ ID NO 105
<211> LENGTH: 36
<212> TYPE: DNA
<213> ORGANISM: Artificial Sequence
<220> FEATURE:
<223> OTHER INFORMATION: probes

<400> SEQUENCE: 105
actacaagat ccgcaagctg acagcggcg gcttct                                     36

<210> SEQ ID NO 106
<211> LENGTH: 36
<212> TYPE: DNA
<213> ORGANISM: Artificial Sequence
<220> FEATURE:
<223> OTHER INFORMATION: probes

<400> SEQUENCE: 106
acaagatccg caagctggac agcggcggct tctaca                                    36

<210> SEQ ID NO 107
<211> LENGTH: 36
<212> TYPE: DNA
<213> ORGANISM: Artificial Sequence
<220> FEATURE:
<223> OTHER INFORMATION: probes

<400> SEQUENCE: 107
agatccgcaa gctggacagc ggcggcttct acatca                                    36

<210> SEQ ID NO 108
<211> LENGTH: 36
<212> TYPE: DNA
<213> ORGANISM: Artificial Sequence
<220> FEATURE:
<223> OTHER INFORMATION: probes

<400> SEQUENCE: 108
tccgcaagct ggacagcggc ggcttctaca tcacct                                    36

<210> SEQ ID NO 109
<211> LENGTH: 36
<212> TYPE: DNA
<213> ORGANISM: Artificial Sequence
<220> FEATURE:
<223> OTHER INFORMATION: probes

<400> SEQUENCE: 109
gcaagctgga cagcggcggc ttctacatca cctccc                             36

<210> SEQ ID NO 110
<211> LENGTH: 36
<212> TYPE: DNA
<213> ORGANISM: Artificial Sequence
<220> FEATURE:
<223> OTHER INFORMATION: probes

<400> SEQUENCE: 110
agctggacag cggcggcttc tacatcacct cccgca                             36

<210> SEQ ID NO 111
<211> LENGTH: 36
<212> TYPE: DNA
<213> ORGANISM: Artificial Sequence
<220> FEATURE:
<223> OTHER INFORMATION: probes

<400> SEQUENCE: 111
tggacagcgg cggcttctac atcacctccc gcaccc                             36

<210> SEQ ID NO 112
<211> LENGTH: 36
<212> TYPE: DNA
<213> ORGANISM: Artificial Sequence
<220> FEATURE:
<223> OTHER INFORMATION: probes

<400> SEQUENCE: 112
acagcggcgg cttctacatc acctcccgca cccagt                             36

<210> SEQ ID NO 113
<211> LENGTH: 36
<212> TYPE: DNA
<213> ORGANISM: Artificial Sequence
<220> FEATURE:
<223> OTHER INFORMATION: probes

<400> SEQUENCE: 113
gcggcggctt ctacatcacc tcccgcaccc agttca                             36

<210> SEQ ID NO 114
<211> LENGTH: 36
<212> TYPE: DNA
<213> ORGANISM: Artificial Sequence
<220> FEATURE:
<223> OTHER INFORMATION: probes

<400> SEQUENCE: 114
gcggcttcta catcacctcc cgcacccagt tcaaca                             36

<210> SEQ ID NO 115
<211> LENGTH: 36
<212> TYPE: DNA
<213> ORGANISM: Artificial Sequence
<220> FEATURE:

<223> OTHER INFORMATION: probes

<400> SEQUENCE: 115
gcttctacat cacctcccgc acccagttca acagcc        36

<210> SEQ ID NO 116
<211> LENGTH: 36
<212> TYPE: DNA
<213> ORGANISM: Artificial Sequence
<220> FEATURE:
<223> OTHER INFORMATION: probes

<400> SEQUENCE: 116
tctacatcac ctcccgcacc cagttcaaca gcctgc        36

<210> SEQ ID NO 117
<211> LENGTH: 36
<212> TYPE: DNA
<213> ORGANISM: Artificial Sequence
<220> FEATURE:
<223> OTHER INFORMATION: probes

<400> SEQUENCE: 117
acatcacctc ccgcacccag ttcaacagcc tgcagc        36

<210> SEQ ID NO 118
<211> LENGTH: 36
<212> TYPE: DNA
<213> ORGANISM: Artificial Sequence
<220> FEATURE:
<223> OTHER INFORMATION: probes

<400> SEQUENCE: 118
tcacctcccg cacccagttc aacagcctgc agcagc        36

<210> SEQ ID NO 119
<211> LENGTH: 36
<212> TYPE: DNA
<213> ORGANISM: Artificial Sequence
<220> FEATURE:
<223> OTHER INFORMATION: probes

<400> SEQUENCE: 119
cctcccgcac ccagttcaac agcctgcagc agctgg        36

<210> SEQ ID NO 120
<211> LENGTH: 36
<212> TYPE: DNA
<213> ORGANISM: Artificial Sequence
<220> FEATURE:
<223> OTHER INFORMATION: probes

<400> SEQUENCE: 120
cccgcaccca gttcaacagc ctgcagcagc tggtgg        36

<210> SEQ ID NO 121
<211> LENGTH: 36
<212> TYPE: DNA
<213> ORGANISM: Artificial Sequence
<220> FEATURE:
<223> OTHER INFORMATION: probes

<400> SEQUENCE: 121
tgccgtgtcc tgacttctgg aatctttgag accaag        36

```
<210> SEQ ID NO 122
<211> LENGTH: 36
<212> TYPE: DNA
<213> ORGANISM: Artificial Sequence
<220> FEATURE:
<223> OTHER INFORMATION: probes

<400> SEQUENCE: 122
cgtgtcctga cttctggaat ctttgagacc aagttc                              36

<210> SEQ ID NO 123
<211> LENGTH: 36
<212> TYPE: DNA
<213> ORGANISM: Artificial Sequence
<220> FEATURE:
<223> OTHER INFORMATION: probes

<400> SEQUENCE: 123
gtcctgactt ctggaatctt tgagaccaag ttccag                              36

<210> SEQ ID NO 124
<211> LENGTH: 36
<212> TYPE: DNA
<213> ORGANISM: Artificial Sequence
<220> FEATURE:
<223> OTHER INFORMATION: probes

<400> SEQUENCE: 124
ctgacttctg gaatctttga gaccaagttc caggtg                              36

<210> SEQ ID NO 125
<211> LENGTH: 36
<212> TYPE: DNA
<213> ORGANISM: Artificial Sequence
<220> FEATURE:
<223> OTHER INFORMATION: probes

<400> SEQUENCE: 125
acttctggaa tctttgagac caagttccag gtggac                              36

<210> SEQ ID NO 126
<211> LENGTH: 36
<212> TYPE: DNA
<213> ORGANISM: Artificial Sequence
<220> FEATURE:
<223> OTHER INFORMATION: probes

<400> SEQUENCE: 126
ggcctgttgc gtctcagcag cagtgcacta aataac                              36

<210> SEQ ID NO 127
<211> LENGTH: 36
<212> TYPE: DNA
<213> ORGANISM: Artificial Sequence
<220> FEATURE:
<223> OTHER INFORMATION: probes

<400> SEQUENCE: 127
ctgttgcgtc tcagcagcag tgcactaaat aacgag                              36

<210> SEQ ID NO 128
<211> LENGTH: 36
<212> TYPE: DNA
<213> ORGANISM: Artificial Sequence
<220> FEATURE:
<223> OTHER INFORMATION: probes
```

<400> SEQUENCE: 128
ttgcgtctca gcagcagtgc actaaataac gagttt                                    36

<210> SEQ ID NO 129
<211> LENGTH: 36
<212> TYPE: DNA
<213> ORGANISM: Artificial Sequence
<220> FEATURE:
<223> OTHER INFORMATION: probes

<400> SEQUENCE: 129
cgtctcagca gcagtgcact aaataacgag tttttt                                    36

<210> SEQ ID NO 130
<211> LENGTH: 36
<212> TYPE: DNA
<213> ORGANISM: Artificial Sequence
<220> FEATURE:
<223> OTHER INFORMATION: probes

<400> SEQUENCE: 130
ctcagcagca gtgcactaaa taacgagttt tttacc                                    36

<210> SEQ ID NO 131
<211> LENGTH: 36
<212> TYPE: DNA
<213> ORGANISM: Artificial Sequence
<220> FEATURE:
<223> OTHER INFORMATION: probes

<400> SEQUENCE: 131
agcagcagtg cactaaataa cgagtttttt acccat                                    36

<210> SEQ ID NO 132
<211> LENGTH: 36
<212> TYPE: DNA
<213> ORGANISM: Artificial Sequence
<220> FEATURE:
<223> OTHER INFORMATION: probes

<400> SEQUENCE: 132
agcagtgcac taaataacga gttttttacc catgcg                                    36

<210> SEQ ID NO 133
<211> LENGTH: 36
<212> TYPE: DNA
<213> ORGANISM: Artificial Sequence
<220> FEATURE:
<223> OTHER INFORMATION: probes

<400> SEQUENCE: 133
agtgcactaa ataacgagtt ttttacccat gcggct                                    36

<210> SEQ ID NO 134
<211> LENGTH: 36
<212> TYPE: DNA
<213> ORGANISM: Artificial Sequence
<220> FEATURE:
<223> OTHER INFORMATION: probes

<400> SEQUENCE: 134
gcactaaata acgagttttt tacccatgcg gctcag                                    36

<210> SEQ ID NO 135
<211> LENGTH: 36

```
<212> TYPE: DNA
<213> ORGANISM: Artificial Sequence
<220> FEATURE:
<223> OTHER INFORMATION: probes

<400> SEQUENCE: 135
ctaaataacg agtttttac ccatgcggct cagagc                                36

<210> SEQ ID NO 136
<211> LENGTH: 36
<212> TYPE: DNA
<213> ORGANISM: Artificial Sequence
<220> FEATURE:
<223> OTHER INFORMATION: probes

<400> SEQUENCE: 136
aataacgagt tttttaccca tgcggctcag agctgg                               36

<210> SEQ ID NO 137
<211> LENGTH: 36
<212> TYPE: DNA
<213> ORGANISM: Artificial Sequence
<220> FEATURE:
<223> OTHER INFORMATION: probes

<400> SEQUENCE: 137
aacgagtttt ttacccatgc ggctcagagc tggcgg                               36

<210> SEQ ID NO 138
<211> LENGTH: 36
<212> TYPE: DNA
<213> ORGANISM: Artificial Sequence
<220> FEATURE:
<223> OTHER INFORMATION: probes

<400> SEQUENCE: 138 gagttttta cccatgcggc tcagagctgg cgggag                                36

<210> SEQ ID NO 139
<211> LENGTH: 36
<212> TYPE: DNA
<213> ORGANISM: Artificial Sequence
<220> FEATURE:
<223> OTHER INFORMATION: probes

<400> SEQUENCE: 139
gtaccaccag ggtggccatc aaaaccctga agcctg                               36

<210> SEQ ID NO 140
<211> LENGTH: 36
<212> TYPE: DNA
<213> ORGANISM: Artificial Sequence
<220> FEATURE:
<223> OTHER INFORMATION: probes

<400> SEQUENCE: 140
ccaccagggt ggccatcaaa accctgaagc ctggca                               36

<210> SEQ ID NO 141
<211> LENGTH: 36
<212> TYPE: DNA
<213> ORGANISM: Artificial Sequence
<220> FEATURE:
<223> OTHER INFORMATION: probes

<400> SEQUENCE: 141
```

```
ccagggtggc catcaaaacc ctgaagcctg gcacga                                 36

<210> SEQ ID NO 142
<211> LENGTH: 96
<212> TYPE: DNA
<213> ORGANISM: Artificial Sequence
<220> FEATURE:
<223> OTHER INFORMATION: probes

<400> SEQUENCE: 142
gggtggccat caaaccctg aagcctggca cgatgtgtgc ctactgcctc tcagtgtctg        60
acttcgacaa cgccagggc ctcaacgtga agcact                                  96

<210> SEQ ID NO 143
<211> LENGTH: 60
<212> TYPE: DNA
<213> ORGANISM: Artificial Sequence
<220> FEATURE:
<223> OTHER INFORMATION: probes

<400> SEQUENCE: 143
cctactgcct ctcagtgtct gacttcgaca acgccaaggg cctcaacgtg aagcactaca       60

<210> SEQ ID NO 144
<211> LENGTH: 60
<212> TYPE: DNA
<213> ORGANISM: Artificial Sequence
<220> FEATURE:
<223> OTHER INFORMATION: probes

<400> SEQUENCE: 144
actgcctctc agtgtctgac ttcgacaacg ccagggcct caacgtgaag cactacaaga       60

<210> SEQ ID NO 145
<211> LENGTH: 60
<212> TYPE: DNA
<213> ORGANISM: Artificial Sequence
<220> FEATURE:
<223> OTHER INFORMATION: probes

<400> SEQUENCE: 145
gcctctcagt gtctgacttc gacaacgcca agggcctcaa cgtgaagcac tacaagatcc       60

<210> SEQ ID NO 146
<211> LENGTH: 60
<212> TYPE: DNA
<213> ORGANISM: Artificial Sequence
<220> FEATURE:
<223> OTHER INFORMATION: probes

<400> SEQUENCE: 146
tctcagtgtc tgacttcgac aacgccaagg gcctcaacgt gaagcactac aagatccgca       60

<210> SEQ ID NO 147
<211> LENGTH: 60
<212> TYPE: DNA
<213> ORGANISM: Artificial Sequence
<220> FEATURE:
<223> OTHER INFORMATION: probes

<400> SEQUENCE: 147
cagtgtctga cttcgacaac gccagggcc tcaacgtgaa gcactacaag atccgcaagc       60

<210> SEQ ID NO 148
<211> LENGTH: 60
```

```
<212> TYPE: DNA
<213> ORGANISM: Artificial Sequence
<220> FEATURE:
<223> OTHER INFORMATION: probes

<400> SEQUENCE: 148
tgtctgactt cgacaacgcc aagggcctca acgtgaagca ctacaagatc cgcaagctgg      60

<210> SEQ ID NO 149
<211> LENGTH: 60
<212> TYPE: DNA
<213> ORGANISM: Artificial Sequence
<220> FEATURE:
<223> OTHER INFORMATION: probes

<400> SEQUENCE: 149
ctgacttcga acgccaag ggcctcaacg tgaagcacta caagatccgc aagctggaca      60

<210> SEQ ID NO 150
<211> LENGTH: 60
<212> TYPE: DNA
<213> ORGANISM: Artificial Sequence
<220> FEATURE:
<223> OTHER INFORMATION: probes

<400> SEQUENCE: 150
acttcgacaa cgccaagggc ctcaacgtga agcactacaa gatccgcaag ctggacagcg      60

<210> SEQ ID NO 151
<211> LENGTH: 60
<212> TYPE: DNA
<213> ORGANISM: Artificial Sequence
<220> FEATURE:
<223> OTHER INFORMATION: probes

<400> SEQUENCE: 151
tcgacaacgc caagggcctc aacgtgaagc actacaagat ccgcaagctg gacagcggcg      60

<210> SEQ ID NO 152
<211> LENGTH: 60
<212> TYPE: DNA
<213> ORGANISM: Artificial Sequence
<220> FEATURE:
<223> OTHER INFORMATION: probes

<400> SEQUENCE: 152
acaacgccaa gggcctcaac gtgaagcact acaagatccg caagctggac agcggcggct      60

<210> SEQ ID NO 153
<211> LENGTH: 60
<212> TYPE: DNA
<213> ORGANISM: Artificial Sequence
<220> FEATURE:
<223> OTHER INFORMATION: probes

<400> SEQUENCE: 153
acgccaaggg cctcaacgtg aagcactaca agatccgcaa gctggacagc ggcggcttct      60

<210> SEQ ID NO 154
<211> LENGTH: 60
<212> TYPE: DNA
<213> ORGANISM: Artificial Sequence
<220> FEATURE:
<223> OTHER INFORMATION: probes

<400> SEQUENCE: 154
```
ccaagggcct caacgtgaag cactacaaga tccgcaagct ggacagcggc ggcttctaca    60

<210> SEQ ID NO 155
<211> LENGTH: 60
<212> TYPE: DNA
<213> ORGANISM: Artificial Sequence
<220> FEATURE:
<223> OTHER INFORMATION: probes

<400> SEQUENCE: 155
agggcctcaa cgtgaagcac tacaagatcc gcaagctgga cagcggcggc ttctacatca    60

<210> SEQ ID NO 156
<211> LENGTH: 60
<212> TYPE: DNA
<213> ORGANISM: Artificial Sequence
<220> FEATURE:
<223> OTHER INFORMATION: probes

<400> SEQUENCE: 156
gcctcaacgt gaagcactac aagatccgca agctggacag cggcggcttc tacatcacct    60

<210> SEQ ID NO 157
<211> LENGTH: 60
<212> TYPE: DNA
<213> ORGANISM: Artificial Sequence
<220> FEATURE:
<223> OTHER INFORMATION: probes

<400> SEQUENCE: 157
tcaacgtgaa gcactacaag atccgcaagc tggacagcgg cggcttctac atcacctccc    60

<210> SEQ ID NO 158
<211> LENGTH: 60
<212> TYPE: DNA
<213> ORGANISM: Artificial Sequence
<220> FEATURE:
<223> OTHER INFORMATION: probes

<400> SEQUENCE: 158
acgtgaagca ctacaagatc cgcaagctgg acagcggcgg cttctacatc acctcccgca    60

<210> SEQ ID NO 159
<211> LENGTH: 60
<212> TYPE: DNA
<213> ORGANISM: Artificial Sequence
<220> FEATURE:
<223> OTHER INFORMATION: probes

<400> SEQUENCE: 159
tgaagcacta caagatccgc aagctggaca gcggcggctt ctacatcacc tcccgcaccc    60

<210> SEQ ID NO 160
<211> LENGTH: 60
<212> TYPE: DNA
<213> ORGANISM: Artificial Sequence
<220> FEATURE:
<223> OTHER INFORMATION: probes

<400> SEQUENCE: 160
agcactacaa gatccgcaag ctggacagcg gcggcttcta catcacctcc cgcacccagt    60

<210> SEQ ID NO 161
<211> LENGTH: 60
<212> TYPE: DNA
<213> ORGANISM: Artificial Sequence
<220> FEATURE:
<223> OTHER INFORMATION: probes

<400> SEQUENCE: 161
actacaagat ccgcaagctg acagcggcg gcttctacat cacctcccgc acccagttca    60

<210> SEQ ID NO 162
<211> LENGTH: 60
<212> TYPE: DNA
<213> ORGANISM: Artificial Sequence
<220> FEATURE:
<223> OTHER INFORMATION: probes

<400> SEQUENCE: 162
acaagatccg caagctggac agcggcggct tctacatcac ctcccgcacc cagttcaaca    60

<210> SEQ ID NO 163
<211> LENGTH: 60
<212> TYPE: DNA
<213> ORGANISM: Artificial Sequence
<220> FEATURE:
<223> OTHER INFORMATION: probes

<400> SEQUENCE: 163
agatccgcaa gctggacagc ggcggcttct acatcacctc ccgcacccag ttcaacagcc    60

<210> SEQ ID NO 164
<211> LENGTH: 60
<212> TYPE: DNA
<213> ORGANISM: Artificial Sequence
<220> FEATURE:
<223> OTHER INFORMATION: probes

<400> SEQUENCE: 164
tccgcaagct ggacagcggc ggcttctaca tcacctcccg cacccagttc aacagcctgc    60

<210> SEQ ID NO 165
<211> LENGTH: 60
<212> TYPE: DNA
<213> ORGANISM: Artificial Sequence
<220> FEATURE:
<223> OTHER INFORMATION: probes

<400> SEQUENCE: 165
gcaagctgga cagcggcggc ttctacatca cctcccgcac ccagttcaac agcctgcagc    60

<210> SEQ ID NO 166
<211> LENGTH: 60
<212> TYPE: DNA
<213> ORGANISM: Artificial Sequence
<220> FEATURE:
<223> OTHER INFORMATION: probes

<400> SEQUENCE: 166
agctggacag cggcggcttc tacatcacct cccgcaccca gttcaacagc ctgcagcagc    60

<210> SEQ ID NO 167
<211> LENGTH: 60
<212> TYPE: DNA
<213> ORGANISM: Artificial Sequence
<220> FEATURE:
<223> OTHER INFORMATION: probes

<400> SEQUENCE: 167
tggacagcgg cggcttctac atcacctccc gcacccagtt caacagcctg cagcagctgg    60

<210> SEQ ID NO 168
<211> LENGTH: 60
<212> TYPE: DNA
<213> ORGANISM: Artificial Sequence
<220> FEATURE:
<223> OTHER INFORMATION: probes

<400> SEQUENCE: 168
acagcggcgg cttctacatc acctcccgca cccagttcaa cagcctgcag cagctggtgg    60

<210> SEQ ID NO 169
<211> LENGTH: 60
<212> TYPE: DNA
<213> ORGANISM: Artificial Sequence
<220> FEATURE:
<223> OTHER INFORMATION: probes

<400> SEQUENCE: 169
gcggcggctt ctacatcacc tcccgcaccc agttcaacag cctgcagcag ctggtggcct    60

<210> SEQ ID NO 170
<211> LENGTH: 60
<212> TYPE: DNA
<213> ORGANISM: Artificial Sequence
<220> FEATURE:
<223> OTHER INFORMATION: probes

<400> SEQUENCE: 170
gcggcttcta catcacctcc cgcacccagt tcaacagcct gcagcagctg gtggcctact    60

<210> SEQ ID NO 171
<211> LENGTH: 60
<212> TYPE: DNA
<213> ORGANISM: Artificial Sequence
<220> FEATURE:
<223> OTHER INFORMATION: probes

<400> SEQUENCE: 171
gcttctacat cacctcccgc acccagttca acagcctgca gcagctggtg gcctactact    60

<210> SEQ ID NO 172
<211> LENGTH: 60
<212> TYPE: DNA
<213> ORGANISM: Artificial Sequence
<220> FEATURE:
<223> OTHER INFORMATION: probes

<400> SEQUENCE: 172
tctacatcac ctcccgcacc cagttcaaca gcctgcagca gctggtggcc tactactcca    60

<210> SEQ ID NO 173
<211> LENGTH: 60
<212> TYPE: DNA
<213> ORGANISM: Artificial Sequence
<220> FEATURE:
<223> OTHER INFORMATION: probes

<400> SEQUENCE: 173
gacctgcttc gctgccgtgt cctgacttct ggaatctttg agaccaagtt ccaggtggac    60

<210> SEQ ID NO 174
<211> LENGTH: 60
<212> TYPE: DNA
<213> ORGANISM: Artificial Sequence
<220> FEATURE:
<223> OTHER INFORMATION: probes

<400> SEQUENCE: 174
ctgcttcgct gccgtgtcct gacttctgga atctttgaga ccaagttcca ggtggacaaa    60

<210> SEQ ID NO 175
<211> LENGTH: 60
<212> TYPE: DNA
<213> ORGANISM: Artificial Sequence
<220> FEATURE:
<223> OTHER INFORMATION: probes

<400> SEQUENCE: 175
cttcgctgcc gtgtcctgac ttctggaatc tttgagacca gttccaggt ggacaaagtc    60

<210> SEQ ID NO 176
<211> LENGTH: 60
<212> TYPE: DNA
<213> ORGANISM: Artificial Sequence
<220> FEATURE:
<223> OTHER INFORMATION: probes

<400> SEQUENCE: 176
cgctgccgtg tcctgacttc tggaatcttt gagaccaagt ccaggtgga caaagtcaac    60

<210> SEQ ID NO 177
<211> LENGTH: 60
<212> TYPE: DNA
<213> ORGANISM: Artificial Sequence
<220> FEATURE:
<223> OTHER INFORMATION: probes

<400> SEQUENCE: 177
tgccgtgtcc tgacttctgg aatctttgag accaagttcc aggtggacaa agtcaacttc    60

<210> SEQ ID NO 178
<211> LENGTH: 60
<212> TYPE: DNA
<213> ORGANISM: Artificial Sequence
<220> FEATURE:
<223> OTHER INFORMATION: probes

<400> SEQUENCE: 178
gtggggacgg atggcctgtt gcgtctcagc agcagtgcac taaataacga gttttttacc    60

<210> SEQ ID NO 179
<211> LENGTH: 60
<212> TYPE: DNA
<213> ORGANISM: Artificial Sequence
<220> FEATURE:
<223> OTHER INFORMATION: probes

<400> SEQUENCE: 179
gggacggatg gcctgttgcg tctcagcagc agtgcactaa ataacgagtt ttttacccat    60

<210> SEQ ID NO 180
<211> LENGTH: 60
<212> TYPE: DNA
<213> ORGANISM: Artificial Sequence
<220> FEATURE:
<223> OTHER INFORMATION: probes

<400> SEQUENCE: 180
acggatggcc tgttgcgtct cagcagcagt gcactaaata cgagttttt tacccatgcg    60

<210> SEQ ID NO 181

```
<211> LENGTH: 60
<212> TYPE: DNA
<213> ORGANISM: Artificial Sequence
<220> FEATURE:
<223> OTHER INFORMATION: probes

<400> SEQUENCE: 181
gatggcctgt tgcgtctcag cagcagtgca ctaaataacg agttttttac ccatgcggct    60

<210> SEQ ID NO 182
<211> LENGTH: 60
<212> TYPE: DNA
<213> ORGANISM: Artificial Sequence
<220> FEATURE:
<223> OTHER INFORMATION: probes

<400> SEQUENCE: 182
ggcctgttgc gtctcagcag cagtgcacta ataacgagt tttttaccca tgcggctcag    60

<210> SEQ ID NO 183
<211> LENGTH: 60
<212> TYPE: DNA
<213> ORGANISM: Artificial Sequence
<220> FEATURE:
<223> OTHER INFORMATION: probes

<400> SEQUENCE: 183
ctgttgcgtc tcagcagcag tgcactaaat aacgagtttt ttacccatgc ggctcagagc    60

<210> SEQ ID NO 184
<211> LENGTH: 60
<212> TYPE: DNA
<213> ORGANISM: Artificial Sequence
<220> FEATURE:
<223> OTHER INFORMATION: probes

<400> SEQUENCE: 184
ttgcgtctca gcagcagtgc actaaataac gagttttta cccatgcggc tcagagctgg    60

<210> SEQ ID NO 185
<211> LENGTH: 60
<212> TYPE: DNA
<213> ORGANISM: Artificial Sequence
<220> FEATURE:
<223> OTHER INFORMATION: probes

<400> SEQUENCE: 185
cgtctcagca gcagtgcact aaataacgag ttttttaccc atgcggctca gagctggcgg    60

<210> SEQ ID NO 186
<211> LENGTH: 60
<212> TYPE: DNA
<213> ORGANISM: Artificial Sequence
<220> FEATURE:
<223> OTHER INFORMATION: probes

<400> SEQUENCE: 186
ctcagcagca gtgcactaaa taacgagttt tttacccatg cggctcagag ctggcgggag    60

<210> SEQ ID NO 187
<211> LENGTH: 60
<212> TYPE: DNA
<213> ORGANISM: Artificial Sequence
<220> FEATURE:
<223> OTHER INFORMATION: probes

<400> SEQUENCE: 187
```
agcagcagtg cactaaataa cgagttttt acccatgcgg ctcagagctg gcgggagcgc    60

<210> SEQ ID NO 188
<211> LENGTH: 60
<212> TYPE: DNA
<213> ORGANISM: Artificial Sequence
<220> FEATURE:
<223> OTHER INFORMATION: probes

<400> SEQUENCE: 188
agcagtgcac taaataacga gttttttacc catgcggctc agagctggcg ggagcgcctg    60

<210> SEQ ID NO 189
<211> LENGTH: 60
<212> TYPE: DNA
<213> ORGANISM: Artificial Sequence
<220> FEATURE:
<223> OTHER INFORMATION: probes

<400> SEQUENCE: 189
agtgcactaa ataacgagtt ttttacccat gcggctcaga gctggcggga gcgcctggct    60

<210> SEQ ID NO 190
<211> LENGTH: 60
<212> TYPE: DNA
<213> ORGANISM: Artificial Sequence
<220> FEATURE:
<223> OTHER INFORMATION: probes

<400> SEQUENCE: 190
gcactaaata acgagttttt tacccatgcg gctcagagct ggcgggagcg cctggctgat    60

<210> SEQ ID NO 191
<211> LENGTH: 60
<212> TYPE: DNA
<213> ORGANISM: Artificial Sequence
<220> FEATURE:
<223> OTHER INFORMATION: probes

<400> SEQUENCE: 191
ggacctggaa cggtaccacc agggtggcca tcaaaaccct gaagcctggc acgatgtctc    60

<210> SEQ ID NO 192
<211> LENGTH: 60
<212> TYPE: DNA
<213> ORGANISM: Artificial Sequence
<220> FEATURE:
<223> OTHER INFORMATION: probes

<400> SEQUENCE: 192
cctggaacgg taccaccagg gtggccatca aaaccctgaa gcctggcacg atgtctccag    60

<210> SEQ ID NO 193
<211> LENGTH: 60
<212> TYPE: DNA
<213> ORGANISM: Artificial Sequence
<220> FEATURE:
<223> OTHER INFORMATION: probes

<400> SEQUENCE: 193
ggaacggtac caccagggtg gccatcaaaa ccctgaagcc tggcacgatg tctccagagg    60

<210> SEQ ID NO 194
<211> LENGTH: 60
<212> TYPE: DNA

```
<213> ORGANISM: Artificial Sequence
<220> FEATURE:
<223> OTHER INFORMATION: probes

<400> SEQUENCE: 194
acggtaccac cagggtggcc atcaaaaccc tgaagcctgg cacgatgtct ccagaggcct    60
```